US007844342B2

(12) United States Patent
Dlugos, Jr. et al.

(10) Patent No.: US 7,844,342 B2
(45) Date of Patent: Nov. 30, 2010

(54) POWERING IMPLANTABLE RESTRICTION SYSTEMS USING LIGHT

(75) Inventors: Daniel F. Dlugos, Jr., Middleton, OH (US); Mark S. Ortiz, Milford, OH (US); David N. Plescia, Cincinnati, OH (US); Michael J. Stokes, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 99 days.

(21) Appl. No.: 12/027,784

(22) Filed: Feb. 7, 2008

(65) Prior Publication Data

US 2009/0204178 A1 Aug. 13, 2009

(51) Int. Cl.
*A61N 1/00* (2006.01)

(52) U.S. Cl. ........ 607/61

(58) Field of Classification Search ........ 600/37; 607/61
See application file for complete search history.

(56) References Cited

U.S. PATENT DOCUMENTS

| | | | |
|---|---|---|---|
| RE3,036 | E | 7/1868 | Shunk |
| RE3,037 | E | 7/1868 | Tucker |
| RE3,115 | E | 9/1868 | Lewis |
| RE3,187 | E | 11/1868 | Winchester |
| RE3,322 | E | 3/1869 | Murch |
| 236,373 | A | 1/1881 | Spilman |
| 322,388 | A | 7/1885 | Lord |
| 400,401 | A | 3/1889 | Gutzkow |
| D23,637 | S | 9/1894 | Casad |
| D24,900 | S | 11/1895 | Clemecet |
| D25,318 | S | 3/1896 | Perky |
| D27,151 | S | 6/1897 | Moulten |
| D29,715 | S | 11/1898 | Wheeler |
| D29,745 | S | 11/1898 | Bunker |
| D29,885 | S | 12/1898 | Gillespie |
| D30,690 | S | 5/1899 | Schwedtmann |
| D30,966 | S | 6/1899 | Howe |
| D31,230 | S | 7/1899 | Hogan |

(Continued)

FOREIGN PATENT DOCUMENTS

CA 1059035 7/1979

(Continued)

OTHER PUBLICATIONS

"Application Specific Integrated Circuits (ASICs)", Honeywell product information from website http://www.honeywell.com/sites/portal?smap=aerospace&page=Radiation-Hardened-Electronics3&theme=T18&catID=CE06BEF88-65F8-6A1E-4ED1-6A1EC1B7AE7A&id=HA0E380D3-C27B-9EBF-AAC8-9FAF8851256D&sel=1&sel4=1; 1 page.

(Continued)

*Primary Examiner*—George Manuel
*Assistant Examiner*—Shubatra Narayanaswamy
(74) *Attorney, Agent, or Firm*—Nutter McClennen & Fish LLP

(57) ABSTRACT

Various powering devices are provided for transferring and/or generating energy from numerous sources to a communicating member implanted in a patient. The energy transferred to or generated by the communicating member can be used to provide power to an implantable restriction system configured to form a restriction in a pathway.

17 Claims, 5 Drawing Sheets

200 201 216 230 240 250 220 210 260

U.S. PATENT DOCUMENTS 689,758 A 12/1901 Shaw
724,913 A 4/1903 Montgomery
899,477 A 9/1908 Williams
926,197 A 6/1909 Kim
953,875 A 4/1910 Waring
991,192 A 5/1911 Battenfeld
1,087,988 A 2/1914 Sheldon
1,210,701 A 1/1917 Ryden
1,219,296 A 3/1917 Hahn
1,224,355 A 5/1917 Brown
1,263,914 A 4/1918 Martin
1,310,290 A 7/1919 Piechowicz
1,384,873 A 7/1921 Strickland
1,421,507 A 7/1922 Lindberg
1,551,525 A 8/1925 Hamer
1,560,973 A 11/1925 Cheron
1,620,633 A 3/1927 Colvin
1,623,403 A 4/1927 Friel
1,689,085 A 10/1928 Russell et al.
1,764,071 A 6/1930 Foulke
1,782,704 A 11/1930 Woodruff
1,807,107 A 5/1931 Sternberch
1,865,446 A 7/1932 Sears
1,882,338 A 10/1932 Reed et al.
1,924,781 A 8/1933 Gaiser
2,027,875 A 1/1936 Odend'hal
2,063,430 A 12/1936 Graser
2,099,160 A 11/1937 Charch
2,105,127 A 1/1938 Petrone
2,106,192 A 1/1938 Saville
2,143,429 A 1/1939 Auble
2,166,603 A 7/1939 Menzer
2,168,427 A 8/1939 McConkey
2,174,525 A 10/1939 Padernal
2,177,564 A 10/1939 Havill
2,178,463 A 10/1939 Bahnson
2,180,599 A 11/1939 Menasco
2,203,460 A 6/1940 Fieber
2,206,038 A 7/1940 Lang Ford
2,216,374 A 10/1940 Martin
2,223,699 A 12/1940 Norgren
2,225,145 A 12/1940 Baumbach
2,225,880 A 12/1940 Montelius
2,261,060 A 10/1941 Giesler
2,261,355 A 11/1941 Flynn
2,295,539 A 9/1942 Beach
2,303,108 A 11/1942 Blackburn
2,303,502 A 12/1942 Rous
2,318,819 A 5/1943 Verson
2,327,407 A 8/1943 Edyvean
2,327,615 A 8/1943 Ankarlo
2,354,571 A 7/1944 Blain
2,426,392 A 8/1947 Fennema
2,426,817 A 9/1947 Charlton et al.
2,440,260 A 4/1948 Gall
2,442,573 A 6/1948 Stafford
2,453,217 A 11/1948 Gregg et al.
2,455,859 A 12/1948 Foley
2,477,922 A 8/1949 Emery et al.
2,478,876 A 8/1949 Nelson
2,482,392 A 9/1949 Whitaker
2,494,881 A 1/1950 Kost
2,509,210 A 5/1950 Clark
2,509,673 A 5/1950 Church
2,511,765 A 6/1950 Bradbury
2,520,056 A 8/1950 Pozun
2,521,976 A 9/1950 Hays
2,533,924 A 12/1950 Foley
2,538,259 A 1/1951 Merriman
2,581,479 A 1/1952 Grashman
2,600,324 A 6/1952 Rappaport
2,606,003 A 8/1952 McNeill
2,615,940 A 10/1952 Williams
2,632,447 A 3/1953 Dobes
2,639,342 A 5/1953 Cope
2,640,119 A 5/1953 Bradford, Jr.
2,641,742 A 6/1953 Wolfe
2,651,304 A 9/1953 Browner
2,665,577 A 1/1954 Sanowskis
2,673,999 A 4/1954 Shey
2,676,609 A 4/1954 Pfarrer
2,684,118 A 7/1954 Osmun
2,689,611 A 9/1954 Martinson
2,697,435 A 12/1954 Ray
2,723,323 A 11/1955 Niemi
2,734,992 A 2/1956 Elliot et al.
2,740,007 A 3/1956 Amelang
2,740,853 A 4/1956 Hatman, Jr.
2,742,323 A 4/1956 Shey
2,747,332 A 5/1956 Morehouse
2,753,876 A 7/1956 Kurt
2,756,883 A 7/1956 Schreck
2,756,983 A 7/1956 Furcini
2,761,603 A 9/1956 Fairchild
2,773,312 A 12/1956 Peck
2,783,728 A 3/1957 Hoffmann
2,787,875 A 4/1957 Johnson
2,793,379 A 5/1957 Moore
2,795,460 A 6/1957 Bletcher
2,804,514 A 8/1957 Peters
2,822,113 A 2/1958 Joiner, Jr.
2,831,478 A 4/1958 Uddenberg, et al.
2,864,393 A 12/1958 Drake
2,865,541 A 12/1958 Hicks
2,870,024 A 1/1959 Martin
2,883,995 A 4/1959 Bialous et al.
2,886,355 A 5/1959 Wurzel
2,895,215 A 7/1959 Neher et al.
2,899,493 A 8/1959 Levine
2,902,861 A 9/1959 Frost et al.
2,923,531 A 2/1960 Bauer et al.
2,924,263 A 2/1960 Landis
2,924,432 A 2/1960 Arps et al
2,930,170 A 3/1960 Holsman et al.
2,938,592 A 5/1960 Charske et al.
2,941,338 A 6/1960 Santschi
2,943,682 A 7/1960 Ingram, Jr. et al.
2,958,781 A 11/1960 Marchal et al.
2,961,479 A 11/1960 Bertling
2,976,355 A 3/1961 Levine
2,976,686 A 3/1961 Stelzer
2,977,876 A 4/1961 Meyers
2,986,715 A 5/1961 Church et al.
2,989,019 A 6/1961 Van Sciver, II
3,010,692 A 11/1961 Jentoft
3,013,234 A 12/1961 Bourns
3,018,791 A 1/1962 Knox
3,034,356 A 5/1962 Bieganski
3,040,800 A 6/1962 Hartley
3,054,618 A 9/1962 Abrams et al.
3,060,262 A 10/1962 Hoer
3,070,373 A 12/1962 Mathews et al.
3,082,414 A 3/1963 Papaminas
3,085,577 A 4/1963 Berman et al.
3,096,410 A 7/1963 Anderson
3,099,262 A 7/1963 Bigliano
3,125,028 A 3/1964 Rohde
3,126,029 A 3/1964 Englesson
3,129,072 A 4/1964 Cook et al.
3,135,914 A 6/1964 Callan et al.
3,144,017 A 8/1964 Muth
3,151,258 A 9/1964 Sonderegger et al.
3,153,460 A 10/1964 Raskin
3,161,051 A 12/1964 Perry, Jr.

| | | | |
|---|---|---|---|
| 3,167,044 | A | 1/1965 | Henrickson |
| 3,171,549 | A | 3/1965 | Orloff |
| 3,172,700 | A | 3/1965 | Haas |
| 3,173,269 | A | 3/1965 | Imbertson |
| 3,182,494 | A | 5/1965 | Beatty et al. |
| 3,187,181 | A | 6/1965 | Keller |
| 3,187,745 | A | 6/1965 | Baum et al. |
| 3,190,388 | A | 6/1965 | Moser et al. |
| 3,205,547 | A | 9/1965 | Riekse |
| 3,208,255 | A | 9/1965 | Burk |
| 3,209,570 | A | 10/1965 | Hills |
| 3,221,468 | A | 12/1965 | Casey |
| 3,228,703 | A | 1/1966 | Wilson |
| 3,229,684 | A | 1/1966 | Nagumo et al. |
| 3,236,088 | A | 2/1966 | Moller |
| 3,238,624 | A | 3/1966 | McCabe |
| 3,240,510 | A | 3/1966 | Spouge |
| 3,245,642 | A | 4/1966 | Dicke |
| 3,255,568 | A | 6/1966 | Martin et al. |
| 3,260,091 | A | 7/1966 | Shaw, Jr. |
| 3,265,822 | A | 8/1966 | Moulten |
| 3,266,487 | A | 8/1966 | Watkins et al. |
| 3,273,447 | A | 9/1966 | Frank |
| 3,283,352 | A | 11/1966 | Hu |
| 3,290,919 | A | 12/1966 | Malinak et al. |
| 3,292,493 | A | 12/1966 | Franklin |
| 3,292,888 | A | 12/1966 | Fischer |
| 3,294,988 | A | 12/1966 | Packard |
| 3,299,603 | A | 1/1967 | Shaw |
| 3,299,882 | A | 1/1967 | Masino |
| 3,301,514 | A | 1/1967 | Sugaya |
| 3,302,457 | A | 2/1967 | Mayes |
| 3,306,384 | A | 2/1967 | Ross |
| 3,313,314 | A | 4/1967 | Burke et al. |
| 3,316,935 | A | 5/1967 | Kaiser et al. |
| 3,320,750 | A | 5/1967 | Haise et al. |
| 3,321,035 | A | 5/1967 | Tarpley |
| 3,332,788 | A | 7/1967 | Barnby |
| 3,334,510 | A | 8/1967 | Hallesy |
| 3,339,401 | A | 9/1967 | Peters |
| 3,340,868 | A | 9/1967 | Darling |
| 3,347,162 | A | 10/1967 | Braznell |
| 3,350,944 | A | 11/1967 | De Michele |
| 3,353,364 | A | 11/1967 | Blanding et al. |
| 3,353,481 | A | 11/1967 | Antonucci |
| 3,356,334 | A | 12/1967 | Scaramucci |
| 3,356,510 | A | 12/1967 | Barnby |
| 3,357,218 | A | 12/1967 | Mitchell |
| 3,357,461 | A | 12/1967 | Friendship |
| 3,359,741 | A | 12/1967 | Nelson |
| 3,361,300 | A | 1/1968 | Kaplan |
| 3,364,929 | A | 1/1968 | Ide et al. |
| 3,365,684 | A | 1/1968 | Stemke |
| 3,378,456 | A | 4/1968 | Roberts |
| 3,380,445 | A | 4/1968 | Frasier |
| 3,380,649 | A | 4/1968 | Roberts |
| 3,385,022 | A | 5/1968 | Anderson |
| 3,389,355 | A | 6/1968 | Schroeder, Jr. |
| 3,393,612 | A | 7/1968 | Gorgens et al. |
| 3,396,561 | A | 8/1968 | Day |
| 3,399,667 | A | 9/1968 | Nishimoto et al. |
| 3,400,734 | A | 9/1968 | Rosenberg |
| 3,403,237 | A | 9/1968 | Wysong |
| 3,409,924 | A | 11/1968 | Slama |
| 3,411,347 | A | 11/1968 | Wirth et al. |
| 3,417,476 | A | 12/1968 | Martens |
| 3,420,325 | A | 1/1969 | McAlister et al. |
| 3,422,324 | A | 1/1969 | Webb |
| 3,426,165 | A | 2/1969 | Beaman |
| 3,438,391 | A | 4/1969 | Yocum |
| 3,443,608 | A | 5/1969 | Copping et al. |
| 3,445,335 | A | 5/1969 | Gluntz |
| 3,447,281 | A | 6/1969 | Bufford, et al. |
| 3,450,153 | A | 6/1969 | Hildebrandt et al. |
| 3,453,546 | A | 7/1969 | Fryer |
| 3,453,848 | A | 7/1969 | Williamson |
| 3,456,134 | A | 7/1969 | Ko |
| 3,457,909 | A | 7/1969 | Laird |
| 3,460,557 | A | 8/1969 | Gallant |
| 3,463,338 | A | 8/1969 | Schneider |
| 3,469,818 | A | 9/1969 | Cowan |
| 3,470,725 | A | 10/1969 | Brown et al. |
| 3,472,230 | A | 10/1969 | Fogarty |
| 3,478,344 | A | 11/1969 | Schwitzgebel et al. |
| 3,482,449 | A | 12/1969 | Werner |
| 3,482,816 | A | 12/1969 | Arnold |
| 3,487,959 | A | 1/1970 | Pearne et al. |
| 3,491,842 | A | 1/1970 | Delacour et al. |
| 3,492,638 | A | 1/1970 | Lane |
| 3,502,829 | A | 3/1970 | Reynolds |
| 3,503,116 | A | 3/1970 | Strack |
| 3,504,664 | A | 4/1970 | Haddad |
| 3,505,808 | A | 4/1970 | Eschle |
| 3,509,754 | A | 5/1970 | Massingill, et al. |
| 3,512,517 | A | 5/1970 | Kadish et al. |
| 3,514,919 | A | 6/1970 | Ashton et al. |
| 3,516,220 | A | 6/1970 | Buford et al. |
| 3,517,553 | A | 6/1970 | Williams et al. |
| 3,527,226 | A | 9/1970 | Hakin et al. |
| 3,529,908 | A | 9/1970 | Smith |
| 3,530,449 | A | 9/1970 | Anderson |
| 3,533,403 | A | 10/1970 | Woodson |
| 3,534,728 | A | 10/1970 | Barrows |
| 3,534,872 | A | 10/1970 | Roth et al. |
| 3,535,914 | A | 10/1970 | Veith et al. |
| 3,539,009 | A | 11/1970 | Kudlaty |
| 3,543,744 | A | 12/1970 | LePar |
| 3,545,275 | A | 12/1970 | Harrison et al. |
| 3,550,583 | A | 12/1970 | Chiku |
| 3,550,847 | A | 12/1970 | Scott |
| 3,563,094 | A | 2/1971 | Rieschel |
| 3,563,245 | A | 2/1971 | McLean et al. |
| 3,566,083 | A | 2/1971 | McMillin |
| 3,566,875 | A | 3/1971 | Stoehr |
| 3,568,367 | A | 3/1971 | Myers |
| 3,568,636 | A | 3/1971 | Lockwood |
| 3,576,554 | A | 4/1971 | Temps, Jr. et al. |
| 3,580,082 | A | 5/1971 | Strack |
| 3,581,402 | A | 6/1971 | London et al |
| 3,583,387 | A | 6/1971 | Garner et al. |
| 3,587,204 | A | 6/1971 | George |
| 3,590,809 | A | 7/1971 | London |
| 3,590,818 | A | 7/1971 | Lemole |
| 3,590,992 | A | 7/1971 | Soderstrom et al. |
| 3,592,183 | A | 7/1971 | Watkins et al. |
| 3,594,519 | A | 7/1971 | Schmidlin |
| 3,602,885 | A | 8/1971 | Grajeda |
| 3,610,016 | A | 10/1971 | Bultman |
| 3,610,851 | A | 10/1971 | Krupski |
| 3,611,811 | A | 10/1971 | Lissau |
| 3,614,926 | A | 10/1971 | Brechtel |
| 3,614,955 | A | 10/1971 | Mirowski et al. |
| 3,619,742 | A | 11/1971 | Rud, Jr. |
| 3,623,371 | A | 11/1971 | Jullien-Davin |
| 3,624,854 | A | 12/1971 | Strong |
| 3,630,242 | A | 12/1971 | Schieser et al. |
| 3,631,847 | A | 1/1972 | Hobbs, II |
| 3,633,881 | A | 1/1972 | Yurdin |
| 3,635,061 | A | 1/1972 | Rydell et al. |
| 3,635,074 | A | 1/1972 | Moos et al. |
| 3,638,496 | A | 2/1972 | King |
| 3,644,883 | A | 2/1972 | Borman et al. |
| 3,648,687 | A | 3/1972 | Ramsey, III |
| 3,651,289 | A | 3/1972 | Nagashima et al. |
| 3,651,405 | A | 3/1972 | Whitney et al. |
| 3,653,671 | A | 4/1972 | Shipes |

3,659,615 A 5/1972 Enger
3,677,685 A 7/1972 Aoki et al.
3,686,958 A 8/1972 Porter et al.
3,688,568 A 9/1972 Karper et al.
3,701,392 A 10/1972 Wirth et al.
3,702,677 A 11/1972 Heffington
3,703,099 A 11/1972 Rouse et al.
3,712,138 A 1/1973 Alinari et al.
3,713,124 A 1/1973 Durland et al.
3,719,524 A 3/1973 Ripley et al.
3,721,412 A 3/1973 Kindorf
3,723,247 A 3/1973 Leine et al.
3,724,000 A 4/1973 Eakman
3,727,463 A 4/1973 Intraub
3,727,616 A 4/1973 Lenzkes
3,730,174 A 5/1973 Madison
3,730,560 A 5/1973 Abildgaard et al.
3,731,679 A 5/1973 Wilhelmson et al.
3,731,681 A 5/1973 Blackshear et al.
3,732,731 A 5/1973 Fussell, Jr.
3,735,040 A 5/1973 Punt et al.
3,736,930 A 6/1973 Georgi
3,738,356 A 6/1973 Workman
3,740,921 A 6/1973 Meyer et al.
3,746,111 A 7/1973 Berthiaume et al.
3,748,678 A 7/1973 Ballou
3,749,098 A 7/1973 De Bennetot et al.
3,749,422 A 7/1973 Abildgaard et al.
3,749,423 A 7/1973 Abildgaard et al.
3,750,194 A 8/1973 Summers
3,757,770 A 9/1973 Brayshaw et al.
3,759,095 A 9/1973 Short, Jr. et al.
3,760,638 A 9/1973 Lawson et al.
3,763,960 A 10/1973 John et al.
3,765,142 A 10/1973 Lindquist et al.
3,765,494 A 10/1973 Kielman, Jr.
3,769,156 A 10/1973 Brecy et al.
3,769,830 A 11/1973 Porter et al.
3,774,243 A 11/1973 Ng et al.
3,776,333 A 12/1973 Mathauser
3,778,051 A 12/1973 Allen et al.
3,780,578 A 12/1973 Sellman et al.
3,781,902 A 12/1973 Shim et al.
3,783,585 A 1/1974 Hoyland et al.
3,789,667 A 2/1974 Porter et al.
3,796,095 A 3/1974 Fussell, Jr.
3,807,219 A 4/1974 Wallskog
3,811,429 A 5/1974 Fletcher et al.
3,815,722 A 6/1974 Sessoms
3,818,765 A 6/1974 Eriksen et al.
3,820,400 A 6/1974 Russo
3,820,795 A 6/1974 Taylor
3,823,610 A 7/1974 Fussell, Jr.
3,825,065 A 7/1974 Lloyd et al.
3,825,963 A 7/1974 Abildgaard et al.
3,825,964 A 7/1974 Groswith, III et al.
3,828,672 A 8/1974 Gazzola et al.
3,828,766 A 8/1974 Krasnow
3,831,588 A 8/1974 Rindner
3,831,942 A 8/1974 Del Mar
3,833,238 A 9/1974 Liard et al.
3,834,167 A 9/1974 Tabor
3,834,739 A 9/1974 Abildgaard et al.
3,835,523 A 9/1974 Stansfield et al.
3,839,708 A 10/1974 Bredesen et al.
3,842,483 A 10/1974 Cramer
3,842,668 A 10/1974 Lippke et al.
3,845,664 A 11/1974 Perry, Jr.
3,845,751 A 11/1974 Runstetler
3,845,757 A 11/1974 Weyer
3,847,434 A 11/1974 Weman et al.
3,850,208 A 11/1974 Hamilton
3,853,117 A 12/1974 Murr
3,854,469 A 12/1974 Giori et al.
3,855,902 A 12/1974 Kirst et al.
3,857,399 A 12/1974 Zacouto et al.
3,857,452 A 12/1974 Hartman
3,857,745 A 12/1974 Grausch et al.
3,858,581 A 1/1975 Kamen
3,863,622 A 2/1975 Buuck
3,863,933 A 2/1975 Tredway
3,867,950 A 2/1975 Fischell
3,868,008 A 2/1975 Brumbaugh
3,868,679 A 2/1975 Arneson
3,871,599 A 3/1975 Takada et al.
3,872,285 A 3/1975 Shum et al.
3,874,388 A 4/1975 King et al.
3,876,980 A 4/1975 Haemmig et al.
3,878,908 A 4/1975 Andersson et al.
3,881,528 A 5/1975 Mackenzie
3,893,111 A 7/1975 Cotter
3,893,451 A 7/1975 Durand et al.
3,895,681 A 7/1975 Griffin et al.
3,899,862 A 8/1975 Muys et al.
3,904,234 A 9/1975 Hill et al.
3,908,334 A 9/1975 Rychiger et al.
3,908,461 A 9/1975 Turpen
3,908,721 A 9/1975 McGahey et al.
3,910,087 A 10/1975 Jones
3,912,168 A 10/1975 Mullins et al.
3,912,304 A 10/1975 Abildgaard et al.
3,918,286 A 11/1975 Whitehead
3,918,291 A 11/1975 Pauly et al.
3,920,965 A 11/1975 Sohrwardy et al.
3,921,682 A 11/1975 McGahey et al.
3,922,951 A 12/1975 Linsinger et al.
3,923,060 A 12/1975 Ellinwood, Jr.
3,924,635 A 12/1975 Hakim et al.
3,928,980 A 12/1975 Ganzinotti et al.
3,929,175 A 12/1975 Coone
3,930,682 A 1/1976 Booth
3,930,852 A 1/1976 Tanaka et al.
3,936,028 A 2/1976 Norton et al.
3,940,122 A 2/1976 Janzen et al.
3,940,630 A 2/1976 Bergonz
3,942,299 A 3/1976 Bory et al.
3,942,382 A 3/1976 Hok et al.
3,942,516 A 3/1976 Glynn et al.
3,942,536 A 3/1976 Mirowski et al.
3,943,915 A 3/1976 Severson
3,945,704 A 3/1976 Kraus et al.
3,946,613 A 3/1976 Silver
3,946,615 A 3/1976 Hluchan
3,946,724 A 3/1976 La Balme et al.
3,948,141 A 4/1976 Shinjo et al.
3,949,388 A 4/1976 Fuller
3,953,289 A 4/1976 Costes et al.
3,954,271 A 5/1976 Tredway, Sr.
3,958,558 A 5/1976 Dunphy et al.
3,961,425 A 6/1976 Swanson et al.
3,961,646 A 6/1976 Schon et al.
3,962,895 A 6/1976 Rydell et al.
3,962,921 A 6/1976 Lips
3,963,019 A 6/1976 Quandt
3,964,485 A 6/1976 Neumeier
3,964,770 A 6/1976 Abildgaard et al.
3,967,737 A 7/1976 Peralta et al.
3,968,473 A 7/1976 Patton et al.
3,968,694 A 7/1976 Clark
3,972,320 A 8/1976 Kalman
3,973,753 A 8/1976 Wheeler
3,973,858 A 8/1976 Poisson et al.
3,974,655 A 8/1976 Halpern et al.
3,974,865 A 8/1976 Fenton et al.
3,977,391 A 8/1976 Fleischmann
3,980,871 A 9/1976 Lindstrom et al.

3,982,571 A 9/1976 Fenton et al.
3,983,948 A 10/1976 Jeter
3,985,133 A 10/1976 Jenkins et al.
3,987,860 A 10/1976 Jabsen
3,989,005 A 11/1976 Bowler, Jr. et al.
3,991,749 A 11/1976 Zent
3,992,948 A 11/1976 D'Antonio et al.
3,993,149 A 11/1976 Harvey
3,996,927 A 12/1976 Frank
3,996,962 A 12/1976 Sutherland
4,003,141 A 1/1977 Le Roy
4,005,282 A 1/1977 Jennings
4,005,593 A 2/1977 Goldberg
4,006,735 A 2/1977 Hittman et al.
4,009,375 A 2/1977 White et al.
4,009,591 A 3/1977 Hester
4,010,449 A 3/1977 Faggin et al.
4,014,319 A 3/1977 Favre et al.
4,014,321 A 3/1977 March
4,016,764 A 4/1977 Rice
4,017,329 A 4/1977 Larson
4,018,134 A 4/1977 Linsinger et al.
4,022,190 A 5/1977 Meyer
4,024,864 A 5/1977 Davies et al.
4,025,912 A 5/1977 Rice
4,026,276 A 5/1977 Chubbuck
4,027,661 A 6/1977 Lyon et al.
4,031,899 A 6/1977 Renirie et al.
4,036,775 A 7/1977 Trautvetter et al.
4,039,069 A 8/1977 Kwan et al.
4,041,954 A 8/1977 Ohara et al.
4,042,504 A 8/1977 Drori et al.
4,045,345 A 8/1977 Drori et al.
4,047,851 A 9/1977 Bender
4,048,494 A 9/1977 Liesting et al.
4,048,879 A 9/1977 Cox
4,049,004 A 9/1977 Walters
4,051,338 A 9/1977 Harris, III
4,052,991 A 10/1977 Zacouto et al.
4,055,074 A 10/1977 Thimons et al.
4,055,175 A 10/1977 Clemens et al.
4,056,854 A 11/1977 Boretos et al.
4,058,007 A 11/1977 Exner et al.
4,062,351 A 12/1977 Hastwell et al.
4,062,354 A 12/1977 Taylor et al.
4,062,360 A 12/1977 Bentley
4,063,439 A 12/1977 Besson et al.
4,064,882 A 12/1977 Johnson et al.
4,070,239 A 1/1978 Bevilacqua
4,072,047 A 2/1978 Reismuller et al.
4,073,292 A 2/1978 Edelman
4,075,099 A 2/1978 Pelton et al.
4,075,602 A 2/1978 Clothier
4,077,072 A 3/1978 Dezura et al.
4,077,394 A 3/1978 McCurdy
4,077,405 A 3/1978 Haerten et al.
4,077,882 A 3/1978 Gangemi
4,078,620 A 3/1978 Westlake et al.
4,080,653 A 3/1978 Barnes, Jr. et al.
4,084,752 A 4/1978 Hagiwara et al.
4,086,488 A 4/1978 Hill
4,087,568 A 5/1978 Fay et al.
4,088,417 A 5/1978 Kosmowski
4,089,329 A 5/1978 Couvillon, Jr. et al.
4,090,802 A 5/1978 Bilz et al.
4,092,719 A 5/1978 Salmon et al.
4,092,925 A 6/1978 Fromson
4,096,866 A 6/1978 Fischell
4,098,293 A 7/1978 Kramer et al.
4,103,496 A 8/1978 Colamussi et al.
4,106,370 A 8/1978 Kraus et al.
4,107,689 A 8/1978 Jellinek
4,107,995 A 8/1978 Ligman et al.
4,108,148 A 8/1978 Cannon, III
4,108,575 A 8/1978 Schal et al.
4,109,148 A 8/1978 Jaulmes et al.
4,109,518 A 8/1978 Dooley et al.
4,109,644 A 8/1978 Kojima
4,111,056 A 9/1978 Mastromatteo
4,111,629 A 9/1978 Nussbaumer et al.
4,114,424 A 9/1978 Johnson
4,114,606 A 9/1978 Seylar
4,120,097 A 10/1978 Jeter
4,120,134 A 10/1978 Scholle
4,121,635 A 10/1978 Hansel
4,123,310 A 10/1978 Varon et al.
4,124,023 A 11/1978 Fleischmann et al.
4,127,110 A 11/1978 Bullara
4,130,169 A 12/1978 Denison
4,131,596 A 12/1978 Allen
4,133,355 A 1/1979 Mayer
4,133,367 A 1/1979 Abell
4,140,131 A 2/1979 Dutcher et al.
4,141,348 A 2/1979 Hittman
4,141,349 A 2/1979 Ory et al.
4,143,661 A 3/1979 LaForge et al.
4,146,029 A 3/1979 Ellinwood, Jr.
4,147,161 A 4/1979 Ikebe et al.
4,148,096 A 4/1979 Haas et al.
4,149,423 A 4/1979 Frosch et al.
4,151,823 A 5/1979 Grosse et al.
4,153,085 A 5/1979 Adams
4,156,422 A 5/1979 Hildebrandt et al.
4,160,448 A 7/1979 Jackson
4,160,971 A 7/1979 Jones et al.
4,166,469 A 9/1979 Littleford
4,167,304 A 9/1979 Gelbke
4,167,952 A 9/1979 Reinicke
4,168,567 A 9/1979 Leguy et al.
4,170,280 A 10/1979 Schwarz
4,171,218 A 10/1979 Hoshino et al.
4,183,124 A 1/1980 Hoffman
4,183,247 A 1/1980 Allen et al.
4,185,641 A 1/1980 Minior et al.
4,186,287 A 1/1980 Scott
4,186,749 A 2/1980 Fryer
4,186,751 A 2/1980 Fleischmann
4,190,057 A 2/1980 Hill et al.
4,191,004 A 3/1980 Gmuer et al.
4,191,187 A 3/1980 Wright et al.
4,192,192 A 3/1980 Schnell
4,193,397 A 3/1980 Tucker et al.
4,204,547 A 5/1980 Allocca
4,206,755 A 6/1980 Klein et al.
4,206,761 A 6/1980 Cosman
4,206,762 A 6/1980 Cosman
4,207,903 A 6/1980 O'Neill
4,212,074 A 7/1980 Kuno et al.
4,217,221 A 8/1980 Masso
4,217,588 A 8/1980 Freeny, Jr.
4,220,189 A 9/1980 Marquez
4,221,219 A 9/1980 Tucker
4,221,523 A 9/1980 Eberle
4,223,837 A 9/1980 Gubbiotti
4,226,124 A 10/1980 Kersten et al.
4,226,229 A 10/1980 Eckhart et al.
4,227,533 A 10/1980 Godfrey
4,231,376 A 11/1980 Lyon et al.
4,232,682 A 11/1980 Veth
4,237,900 A 12/1980 Schulman et al.
4,241,247 A 12/1980 Byrne et al.
4,241,870 A 12/1980 Marcus
4,245,593 A 1/1981 Stein
4,246,877 A 1/1981 Kennedy
4,247,850 A 1/1981 Marcus
4,248,238 A 2/1981 Joseph et al.

4,248,241 A 2/1981 Tacchi
4,256,094 A 3/1981 Kapp et al.
4,256,118 A 3/1981 Nagel et al.
4,262,343 A 4/1981 Claycomb
4,262,632 A 4/1981 Hanton et al.
4,265,241 A 5/1981 Portner et al.
4,265,252 A 5/1981 Chubbuck et al.
4,271,018 A 6/1981 Drori et al.
4,273,070 A 6/1981 Hoefelmayr et al.
4,274,444 A 6/1981 Ruyak
4,275,600 A 6/1981 Turner et al.
4,275,913 A 6/1981 Marcus
4,278,540 A 7/1981 Drori et al.
4,280,036 A 7/1981 Fukatsu et al.
4,280,775 A 7/1981 Wood
4,281,666 A 8/1981 Cosman
4,281,667 A 8/1981 Cosman
4,284,073 A 8/1981 Krause et al.
4,285,770 A 8/1981 Chi et al.
4,291,699 A 9/1981 Geddes et al.
4,295,963 A 10/1981 Drori et al.
4,297,927 A 11/1981 Kuroda et al.
4,303,075 A 12/1981 Heilman et al.
4,305,402 A 12/1981 Katims
4,312,374 A 1/1982 Drori et al.
4,314,480 A 2/1982 Becker
4,316,693 A 2/1982 Baxter et al.
4,325,387 A 4/1982 Helfer
4,327,804 A 5/1982 Reed
4,328,654 A 5/1982 Van Ginkel et al.
4,332,254 A 6/1982 Lundquist
4,339,831 A 7/1982 Johnson
4,342,218 A 8/1982 Fox
4,342,308 A 8/1982 Trick
4,346,604 A 8/1982 Snook et al.
4,347,851 A 9/1982 Jundanian
4,350,647 A 9/1982 de la Cruz
4,350,970 A 9/1982 von Tomkewitsch et al.
4,351,037 A 9/1982 Scherbatskoy
4,351,116 A 9/1982 Scott, Jr.
4,356,486 A 10/1982 Mount
4,360,010 A 11/1982 Finney
4,360,277 A 11/1982 Daniel et al.
4,361,153 A 11/1982 Slocum et al.
4,363,236 A 12/1982 Meyers
4,364,276 A 12/1982 Shimazoe et al.
4,365,425 A 12/1982 Gotchel
4,368,937 A 1/1983 Palombo et al.
4,369,013 A 1/1983 Abildgaard et al.
4,373,527 A 2/1983 Fischell
4,376,523 A 3/1983 Goyen et al.
4,378,809 A 4/1983 Cosman
4,380,427 A 4/1983 Hehl et al.
4,385,636 A 5/1983 Cosman
4,386,422 A 5/1983 Mumby et al.
4,387,907 A 6/1983 Hiestand et al.
4,392,368 A 7/1983 Folkesson et al.
4,393,899 A 7/1983 Tsuji et al.
4,393,951 A 7/1983 Horst-Rudolf et al.
4,395,232 A 7/1983 Koch
4,395,258 A 7/1983 Wang et al.
4,395,916 A 8/1983 Martin
4,398,983 A 8/1983 Suzuki et al.
4,399,705 A 8/1983 Weiger et al.
4,399,707 A 8/1983 Wamstad
4,399,809 A 8/1983 Baro et al.
4,399,821 A 8/1983 Bowers
4,403,984 A 9/1983 Ash et al.
4,404,968 A 9/1983 Evans, Sr.
4,404,974 A 9/1983 Titus
4,405,318 A 9/1983 Whitney et al.
4,407,125 A 10/1983 Parsons et al.
4,407,271 A 10/1983 Schiff
4,407,296 A 10/1983 Anderson
4,407,326 A 10/1983 Wilhelm
4,408,597 A 10/1983 Tenney, Jr.
4,408,615 A 10/1983 Grossman
4,415,071 A 11/1983 Butler et al.
4,416,282 A 11/1983 Saulson et al.
4,418,899 A 12/1983 Zimmermann et al.
4,419,393 A 12/1983 Hanson et al.
4,421,505 A 12/1983 Schwartz
4,424,720 A 1/1984 Bucchianeri
4,428,228 A 1/1984 Banzhaf et al.
4,428,365 A 1/1984 Hakky et al.
4,430,899 A 2/1984 Wessel et al.
4,431,009 A 2/1984 Marino, Jr. et al.
4,431,365 A 2/1984 Sturtz, Jr.
4,432,363 A 2/1984 Kakegawa et al.
4,435,173 A 3/1984 Siposs et al.
4,439,186 A 3/1984 Kuhl et al.
4,441,491 A 4/1984 Evans, Sr.
4,441,501 A 4/1984 Parent
4,444,194 A 4/1984 Burcham
4,444,498 A 4/1984 Heinemann
4,445,385 A 5/1984 Endo
4,446,711 A 5/1984 Valente
4,447,224 A 5/1984 DeCant, Jr. et al.
4,449,493 A 5/1984 Kopec et al.
4,450,811 A 5/1984 Ichikawa et al.
4,451,033 A 5/1984 Nestegard
4,453,537 A 6/1984 Spitzer
4,453,578 A 6/1984 Wilder
4,460,835 A 7/1984 Masuoka et al.
4,464,170 A 8/1984 Clemens et al.
4,465,015 A 8/1984 Osta et al.
4,465,474 A 8/1984 Mardorf et al.
4,466,290 A 8/1984 Frick
4,468,172 A 8/1984 Dixon et al.
4,468,762 A 8/1984 Jurgens et al.
4,469,365 A 9/1984 Marcus et al.
4,471,182 A 9/1984 Wielgos et al.
4,471,786 A 9/1984 Inagaki et al.
4,473,067 A 9/1984 Schiff
4,473,078 A 9/1984 Angel
4,476,721 A 10/1984 Hochreuther et al.
4,478,213 A 10/1984 Redding
4,478,538 A 10/1984 Kakino et al.
4,483,196 A 11/1984 Kurtz et al.
4,484,135 A 11/1984 Ishihara et al.
4,485,813 A 12/1984 Anderson et al.
4,489,916 A 12/1984 Stevens
4,492,632 A 1/1985 Mattson
4,494,411 A 1/1985 Koschke et al.
4,494,950 A 1/1985 Fischell
4,497,176 A 2/1985 Rubin et al.
4,497,201 A 2/1985 Allen et al.
4,499,394 A 2/1985 Koal
4,499,691 A 2/1985 Karazim et al.
4,499,750 A 2/1985 Gerber et al.
4,503,678 A 3/1985 Wimbush et al.
4,511,974 A 4/1985 Nakane et al.
4,513,295 A 4/1985 Jones et al.
4,515,004 A 5/1985 Jaenson
4,515,750 A 5/1985 Pardini et al.
4,516,866 A 5/1985 Yamauchi et al.
4,518,637 A 5/1985 Takeda et al.
4,519,401 A 5/1985 Ko et al.
4,520,443 A 5/1985 Yuki et al.
4,522,213 A 6/1985 Wallroth et al.
4,527,568 A 7/1985 Rickards et al.
4,529,401 A 7/1985 Leslie et al.
4,531,526 A 7/1985 Genest
4,531,936 A 7/1985 Gordon
4,536,000 A 8/1985 Rohm et al.
4,537,005 A 8/1985 Hoyland et al.

4,537,129 A 8/1985 Heinemann et al.
4,538,616 A 9/1985 Rogoff
4,540,404 A 9/1985 Wolvek
4,542,461 A 9/1985 Eldridge et al.
4,544,369 A 10/1985 Skakoon et al.
4,545,185 A 10/1985 Chikatani et al.
4,546,524 A 10/1985 Kreft
4,548,209 A 10/1985 Wielders et al.
4,552,150 A 11/1985 Zacouto et al.
4,553,226 A 11/1985 Scherbatskoy
4,556,063 A 12/1985 Thompson et al.
4,557,269 A 12/1985 Reynolds et al.
4,557,332 A 12/1985 Denison et al.
4,559,815 A 12/1985 Needham et al.
4,560,979 A 12/1985 Rosskopf et al.
4,561,442 A 12/1985 Vollmann et al.
4,562,751 A 1/1986 Nason et al.
4,563,175 A 1/1986 LaFond
4,565,116 A 1/1986 Hehl et al.
4,566,456 A 1/1986 Koning et al.
4,569,623 A 2/1986 Goldmann
4,570,351 A 2/1986 Szanto et al.
4,571,161 A 2/1986 Leblanc et al.
4,571,995 A 2/1986 Timme
4,573,835 A 3/1986 Eckardt et al.
4,574,792 A 3/1986 Trick
4,576,181 A 3/1986 Wallace et al.
4,576,183 A 3/1986 Plicchi et al.
4,577,512 A 3/1986 Lowenheck et al.
4,581,018 A 4/1986 Jassawalla et al.
4,581,915 A 4/1986 Haulsee et al.
4,587,840 A 5/1986 Dobler et al.
4,589,805 A 5/1986 Duffner et al.
4,592,339 A 6/1986 Kuzmak et al.
4,592,340 A 6/1986 Boyles
4,593,703 A 6/1986 Cosman
4,595,228 A 6/1986 Chu
4,596,563 A 6/1986 Pande
4,599,943 A 7/1986 Kobler et al.
4,600,855 A 7/1986 Strachan et al.
4,602,541 A 7/1986 Benzinger et al.
4,604,089 A 8/1986 Santangelo et al.
4,605,354 A 8/1986 Daly
4,606,419 A 8/1986 Perini
4,606,478 A 8/1986 Hack et al.
4,610,256 A 9/1986 Wallace
4,614,137 A 9/1986 Jones
4,617,016 A 10/1986 Blomberg et al.
4,618,861 A 10/1986 Gettens et al.
4,620,807 A 11/1986 Polit
4,621,331 A 11/1986 Iwata et al.
4,622,871 A 11/1986 Van Sickle et al.
4,626,462 A 12/1986 Kober et al.
4,633,304 A 12/1986 Nagasaki et al.
4,633,878 A 1/1987 Bombardieri et al.
4,635,182 A 1/1987 Hintz
4,637,736 A 1/1987 Andeen et al.
4,638,665 A 1/1987 Benson et al.
4,644,246 A 2/1987 Knapen et al.
4,646,553 A 3/1987 Tufte et al.
4,648,363 A 3/1987 Kronich
4,648,406 A 3/1987 Miller
4,658,358 A 4/1987 Leach et al.
4,658,760 A 4/1987 Zebuhr
4,660,568 A 4/1987 Cosman
4,665,511 A 5/1987 Rodney et al.
4,665,896 A 5/1987 LaForge et al.
4,669,484 A 6/1987 Masters
4,672,974 A 6/1987 Lee
4,674,457 A 6/1987 Berger et al.
4,674,546 A 6/1987 Fournier et al.
4,678,408 A 7/1987 Nason et al.
4,681,559 A 7/1987 Hooven
4,683,850 A 8/1987 Bauder et al.
4,685,463 A 8/1987 Williams
4,685,469 A 8/1987 Keller et al.
4,685,903 A 8/1987 Cable et al.
4,686,987 A 8/1987 Salo et al.
4,687,530 A 8/1987 Berscheid et al.
4,689,979 A 9/1987 Otsuka et al.
4,691,694 A 9/1987 Boyd et al.
4,691,710 A 9/1987 Dickens et al.
4,693,253 A 9/1987 Adams
4,695,237 A 9/1987 Inaba et al.
4,696,189 A 9/1987 Hochreuther et al.
4,697,574 A 10/1987 Karcher et al.
4,698,038 A 10/1987 Key et al.
4,700,497 A 10/1987 Sato et al.
4,700,610 A 10/1987 Bauer et al.
4,701,143 A 10/1987 Key et al.
4,703,756 A 11/1987 Gough et al.
4,705,507 A 11/1987 Boyles
4,706,948 A 11/1987 Kroecher et al.
4,712,562 A 12/1987 Ohayon et al.
4,718,425 A 1/1988 Tanaka et al.
4,722,348 A 2/1988 Ligtenberg et al.
4,724,806 A 2/1988 Hartwig et al.
4,724,830 A 2/1988 Fischell
4,725,826 A 2/1988 Hunter
4,728,479 A 3/1988 Merkovsky
4,729,517 A 3/1988 Krokor et al.
4,730,188 A 3/1988 Milheiser
4,730,420 A 3/1988 Stratmann et al.
4,730,619 A 3/1988 Koning et al.
4,731,058 A 3/1988 Doan
4,735,205 A 4/1988 Chachques et al.
4,738,267 A 4/1988 Lazorthes et al.
4,738,268 A 4/1988 Kipnis
4,741,345 A 5/1988 Matthews et al.
4,741,732 A 5/1988 Crankshaw et al.
4,743,129 A 5/1988 Keryhuel et al.
4,745,541 A 5/1988 Vaniglia et al.
4,746,830 A 5/1988 Holland
4,750,495 A 6/1988 Moore et al.
4,752,115 A 6/1988 Murray, Jr. et al.
4,752,658 A 6/1988 Mack
4,757,463 A 7/1988 Ballou et al.
4,759,386 A 7/1988 Grouw, III
4,763,649 A 8/1988 Merrick
4,765,001 A 8/1988 Smith
4,767,406 A 8/1988 Wadham et al.
4,769,001 A 9/1988 Prince
4,772,896 A 9/1988 Nakatsu et al.
4,773,401 A 9/1988 Citak et al.
4,774,950 A 10/1988 Cohen
4,774,955 A 10/1988 Jones
4,777,953 A 10/1988 Ash et al.
4,779,626 A 10/1988 Peel et al.
4,781,192 A 11/1988 Demer
4,782,826 A 11/1988 Fogarty
4,783,106 A 11/1988 Nutter
4,788,847 A 12/1988 Sterghos
4,791,318 A 12/1988 Lewis et al.
4,794,803 A 1/1989 Osterhout et al.
4,796,641 A 1/1989 Mills et al.
4,798,211 A 1/1989 Goor et al.
4,798,227 A 1/1989 Goodwin
4,799,491 A 1/1989 Eckerle
4,799,625 A 1/1989 Weaver, Jr. et al.
4,802,488 A 2/1989 Eckerle
4,803,987 A 2/1989 Calfee et al.
4,804,368 A 2/1989 Skakoon et al.
4,807,321 A 2/1989 Grasselli et al.
4,808,167 A 2/1989 Mann et al.
4,812,823 A 3/1989 Dickerson
4,819,656 A 4/1989 Spector 4,820,265 A 4/1989 DeSatnick et al.
4,820,953 A 4/1989 Saubolle et al.
4,821,167 A 4/1989 Wiebe
4,821,723 A 4/1989 Baker, Jr. et al.
4,823,779 A 4/1989 Daly et al.
4,830,006 A 5/1989 Haluska et al.
4,832,034 A 5/1989 Pizziconi et al.
4,833,384 A 5/1989 Munro et al.
4,834,731 A 5/1989 Nowak et al.
4,838,857 A 6/1989 Strowe et al.
4,840,068 A 6/1989 Mayhew, Jr.
4,840,350 A 6/1989 Cook et al.
4,844,002 A 7/1989 Yasui et al.
4,846,153 A 7/1989 Berci
4,846,191 A 7/1989 Brockway et al.
4,846,664 A 7/1989 Hehl et al.
4,854,328 A 8/1989 Pollack
4,863,470 A 9/1989 Carter
4,865,587 A 9/1989 Walling
4,867,160 A 9/1989 Schaldach et al.
4,867,498 A 9/1989 Delphia et al.
4,867,618 A 9/1989 Brohammer
4,869,252 A 9/1989 Gilli
4,870,258 A 9/1989 Mochizuki et al.
4,871,351 A 10/1989 Feingold et al.
4,872,483 A 10/1989 Shah
4,872,869 A 10/1989 Johns
4,873,677 A 10/1989 Sakamoto et al.
4,875,483 A 10/1989 Vollmann et al.
4,880,004 A 11/1989 Baker, Jr. et al.
4,882,678 A 11/1989 Hollis et al.
4,886,392 A 12/1989 Iio et al.
4,895,151 A 1/1990 Grevis et al.
4,896,594 A 1/1990 Baur et al.
4,898,158 A 2/1990 Daly et al.
4,898,578 A 2/1990 Rubalcaba, Jr.
4,899,751 A 2/1990 Cohen
4,899,752 A 2/1990 Cohen
4,902,277 A 2/1990 Mathies et al.
4,903,701 A 2/1990 Moore et al.
4,909,678 A 3/1990 Kakimoto et al.
4,913,147 A 4/1990 Fahlstrom et al.
4,919,143 A 4/1990 Ayers
4,924,872 A 5/1990 Frank
4,926,903 A 5/1990 Kawai et al.
4,932,406 A 6/1990 Berkovits
4,934,369 A 6/1990 Maxwell
4,936,304 A 6/1990 Kresh et al.
4,940,037 A 7/1990 Eckert et al.
4,941,718 A 7/1990 Alexander, III et al.
4,942,004 A 7/1990 Catanzaro
4,944,050 A 7/1990 Shames et al.
4,944,298 A 7/1990 Sholder
4,944,307 A 7/1990 Hon et al.
4,945,761 A 8/1990 Lessi et al.
4,949,724 A 8/1990 Mahutte et al.
4,952,205 A 8/1990 Mauerer et al.
4,952,928 A 8/1990 Carroll et al.
4,953,563 A 9/1990 Kaiser et al.
4,954,677 A 9/1990 Alberter et al.
4,958,630 A 9/1990 Rosenbluth et al.
4,958,645 A 9/1990 Cadell et al.
4,960,424 A 10/1990 Grooters
4,960,966 A 10/1990 Evans et al.
4,967,585 A 11/1990 Grimaldo
4,967,761 A 11/1990 Nathanielsz
4,970,823 A 11/1990 Chen et al.
4,971,251 A 11/1990 Dobrick et al.
4,977,896 A 12/1990 Robinson et al.
4,978,335 A 12/1990 Arthur, III
4,978,338 A 12/1990 Melsky et al.
4,979,730 A 12/1990 Holbrook et al.
4,980,671 A 12/1990 McCurdy
4,981,141 A 1/1991 Segalowitz
4,981,173 A 1/1991 Perkins et al.
4,981,426 A 1/1991 Aoki et al.
4,987,897 A 1/1991 Funke et al.
4,988,337 A 1/1991 Ito et al.
4,992,794 A 2/1991 Brouwers et al.
4,997,556 A 3/1991 Yano et al.
5,001,528 A 3/1991 Bahraman
5,003,807 A 4/1991 Terrell et al.
5,003,975 A 4/1991 Hafelfinger et al.
5,003,976 A 4/1991 Alt et al.
5,004,472 A 4/1991 Wallace
5,004,873 A 4/1991 Schnut
5,005,574 A 4/1991 Fearnot et al.
5,005,586 A 4/1991 Lahr
5,006,844 A 4/1991 Ohta et al.
5,007,401 A 4/1991 Grohn et al.
5,007,430 A 4/1991 Dardik
5,007,919 A 4/1991 Silva et al.
5,009,662 A 4/1991 Wallace et al.
5,010,893 A 4/1991 Sholder
5,012,286 A 4/1991 Kawano et al.
5,012,810 A 5/1991 Strand et al.
5,013,292 A 5/1991 Lemay et al.
5,014,040 A 5/1991 Weaver et al.
5,019,032 A 5/1991 Robertson
5,019,041 A 5/1991 Robinson et al.
5,020,845 A 6/1991 Falcoff et al.
5,021,046 A 6/1991 Wallace
5,022,395 A 6/1991 Russie
5,024,965 A 6/1991 Chang et al.
5,026,180 A 6/1991 Tajima et al.
5,026,360 A 6/1991 Johnsen et al.
5,028,918 A 7/1991 Giles et al.
5,032,822 A 7/1991 Sweet
5,036,869 A 8/1991 Inahara et al.
5,038,800 A 8/1991 Oba et al.
5,041,086 A 8/1991 Koenig et al.
5,041,826 A 8/1991 Milheiser
5,042,503 A 8/1991 Torok et al.
5,044,770 A 9/1991 Haghkar
5,046,661 A 9/1991 Kimura et al.
5,048,060 A 9/1991 Arai et al.
5,050,922 A 9/1991 Falcoff
5,052,910 A 10/1991 Hehl et al.
5,053,008 A 10/1991 Bajaj
5,057,078 A 10/1991 Foote et al.
5,058,583 A 10/1991 Geddes et al.
5,061,239 A 10/1991 Shiels
5,062,052 A 10/1991 Sparer et al.
5,062,053 A 10/1991 Shirai et al.
5,062,559 A 11/1991 Falcoff
5,064,974 A 11/1991 Vigneau et al.
5,067,960 A 11/1991 Grandjean et al.
5,068,779 A 11/1991 Sullivan et al.
5,069,680 A 12/1991 Grandjean et al.
5,077,102 A 12/1991 Chong
5,077,870 A 1/1992 Melbye et al.
5,078,139 A 1/1992 Strand et al.
5,082,006 A 1/1992 Jonasson et al.
5,083,563 A 1/1992 Collins et al.
5,084,699 A 1/1992 DeMichele
5,085,224 A 2/1992 Galen et al.
5,085,258 A 2/1992 Fink, Jr. et al.
5,089,673 A 2/1992 Strzodka et al.
5,089,979 A 2/1992 McEachern et al.
5,095,309 A 3/1992 Troyk et al.
5,096,271 A 3/1992 Portman
5,097,831 A 3/1992 Lekholm
5,098,384 A 3/1992 Abrams
5,103,832 A 4/1992 Jackson
5,105,810 A 4/1992 Collins et al.
5,107,850 A 4/1992 Olive 5,112,344 A 5/1992 Petros
5,113,859 A 5/1992 Funke et al.
5,113,869 A 5/1992 Nappholz et al.
5,115,676 A 5/1992 Lee
5,117,825 A 6/1992 Grevious
5,121,777 A 6/1992 Leininger et al.
5,127,451 A 7/1992 Fink, Jr. et al.
5,129,394 A 7/1992 Mehra
5,129,806 A 7/1992 Hehl et al.
5,131,145 A 7/1992 Badoureaux et al.
5,131,388 A 7/1992 Pless et al.
5,133,358 A 7/1992 Gustafson et al.
5,135,488 A 8/1992 Foote et al.
5,139,484 A 8/1992 Hazon et al.
5,144,949 A 9/1992 Olson
5,148,580 A 9/1992 Dyckow et al.
5,148,695 A 9/1992 Ellis
5,152,770 A 10/1992 Bengmark et al.
5,152,776 A 10/1992 Pinchuk
5,154,170 A 10/1992 Bennett et al.
5,154,171 A 10/1992 Chirife et al.
5,154,693 A 10/1992 East et al.
5,156,972 A 10/1992 Issachar et al.
5,158,078 A 10/1992 Bennett et al.
5,163,429 A 11/1992 Cohen
5,167,615 A 12/1992 East et al.
5,168,757 A 12/1992 Rabenau et al.
5,168,982 A 12/1992 Hakanen et al.
5,171,299 A 12/1992 Heitzmann et al.
5,173,873 A 12/1992 Wu et al.
5,174,286 A 12/1992 Chirife et al.
5,174,291 A 12/1992 Schoonen et al.
5,176,502 A 1/1993 Sanderson et al.
5,178,197 A 1/1993 Healy
5,181,423 A 1/1993 Philipps et al.
5,181,517 A 1/1993 Hickey
5,184,132 A 2/1993 Baird
5,184,614 A 2/1993 Collins et al.
5,184,619 A 2/1993 Austin
5,185,535 A 2/1993 Farb et al.
5,186,224 A 2/1993 Schirmacher et al.
5,188,106 A 2/1993 Nappholz et al.
5,188,604 A 2/1993 Orth
5,192,314 A 3/1993 Daskalakis
5,195,362 A 3/1993 Eason
5,197,322 A 3/1993 Indravudh
5,199,427 A 4/1993 Strickland
5,199,428 A 4/1993 Obel et al.
5,201,753 A 4/1993 Lampropoulos et al.
5,204,670 A 4/1993 Stinton
5,207,429 A 5/1993 Walmsley et al.
5,209,223 A 5/1993 McGorry et al.
5,209,732 A 5/1993 Lampropoulos et al.
5,211,129 A 5/1993 Taylor et al.
5,211,161 A 5/1993 Stef et al.
5,212,476 A 5/1993 Maloney
5,213,331 A 5/1993 Avanzini
5,215,523 A 6/1993 Williams et al.
5,218,343 A 6/1993 Stobbe et al.
5,218,957 A 6/1993 Strickland
5,226,429 A 7/1993 Kuzmak
5,226,604 A 7/1993 Seiffert et al.
5,230,694 A 7/1993 Rosenblum
5,233,985 A 8/1993 Hudrlik
5,235,326 A 8/1993 Beigel et al.
5,244,269 A 9/1993 Harriehausen et al.
5,244,461 A 9/1993 Derlien et al.
5,246,008 A 9/1993 Mueller et al.
5,249,858 A 10/1993 Nusser
5,250,020 A 10/1993 Bley
5,254,096 A 10/1993 Rondelet et al.
5,256,157 A 10/1993 Samiotes et al.
5,263,244 A 11/1993 Centa et al.
5,263,981 A 11/1993 Polyak et al.
5,267,940 A 12/1993 Moulder
5,267,942 A 12/1993 Saperston
5,269,891 A 12/1993 Colin et al.
5,271,395 A 12/1993 Wahlstrand et al.
5,274,859 A 1/1994 Redman et al.
5,280,789 A 1/1994 Potts
5,282,839 A 2/1994 Roline et al.
5,282,840 A 2/1994 Hudrlik
5,291,894 A 3/1994 Nagy et al.
5,292,219 A 3/1994 Merin et al.
5,295,967 A 3/1994 Rondelet et al.
5,298,022 A 3/1994 Bernardi et al.
5,298,884 A 3/1994 Gilmore et al.
5,300,093 A 4/1994 Koestner et al.
5,300,120 A 4/1994 Knapp et al.
5,304,112 A 4/1994 Mrklas et al.
5,305,923 A 4/1994 Kirschner et al.
5,312,443 A 5/1994 Adams et al.
5,312,452 A 5/1994 Salo
5,312,453 A 5/1994 Shelton et al.
5,313,953 A 5/1994 Yomtov et al.
5,314,451 A 5/1994 Mulier
5,314,457 A 5/1994 Jeutter et al.
5,324,315 A 6/1994 Grevious
5,325,834 A 7/1994 Ballheimer et al.
5,326,249 A 7/1994 Weissfloch et al.
5,328,460 A 7/1994 Lord et al.
5,330,511 A 7/1994 Boute et al.
5,337,750 A 8/1994 Walloch
5,341,430 A 8/1994 Aulia et al.
5,342,401 A 8/1994 Spano et al.
5,342,406 A 8/1994 Thompson
5,344,388 A 9/1994 Maxwell et al.
5,347,476 A 9/1994 McBean, Sr.
5,348,210 A 9/1994 Linzell et al.
5,348,536 A 9/1994 Young et al.
5,350,413 A 9/1994 Miller et al.
5,352,180 A 10/1994 Candelon et al.
5,353,622 A 10/1994 Theener
5,353,800 A 10/1994 Pohndorf et al.
5,354,200 A 10/1994 Klein et al.
5,354,316 A 10/1994 Keimel
5,354,319 A 10/1994 Wyborny et al.
5,360,407 A 11/1994 Leonard et al.
5,365,462 A 11/1994 McBean, Sr.
5,365,619 A 11/1994 Solomon
5,365,985 A 11/1994 Todd et al.
5,368,040 A 11/1994 Carney
5,370,665 A 12/1994 Hudrlik
5,373,852 A 12/1994 Harrison et al.
5,375,073 A 12/1994 McBean
5,377,128 A 12/1994 McBean
5,378,231 A 1/1995 Johnson et al.
5,382,232 A 1/1995 Hague et al.
5,383,915 A 1/1995 Adams
5,388,578 A 2/1995 Yomtov et al.
5,388,586 A 2/1995 Lee et al.
5,388,831 A 2/1995 Quadri et al.
5,394,909 A 3/1995 Mitchell et al.
5,402,944 A 4/1995 Pape et al.
5,406,957 A 4/1995 Tansey
5,409,009 A 4/1995 Olson
5,411,031 A 5/1995 Yomtov
5,411,551 A 5/1995 Winston et al.
5,411,552 A 5/1995 Andersen et al.
5,416,372 A 5/1995 Ljungstroem et al.
5,417,226 A 5/1995 Juma
5,417,717 A 5/1995 Salo et al.
5,425,362 A 6/1995 Siker et al.
5,431,171 A 7/1995 Harrison et al.
5,431,694 A 7/1995 Snaper et al.
5,433,694 A 7/1995 Lim et al.

5,437,605 A 8/1995 Helmy et al.
5,443,215 A 8/1995 Fackler
5,447,519 A 9/1995 Peterson
5,449,368 A 9/1995 Kuzmak
5,456,690 A 10/1995 Duong-Van
5,461,390 A 10/1995 Hoshen
5,464,435 A 11/1995 Neumann
5,467,627 A 11/1995 Smith et al.
5,474,226 A 12/1995 Joseph
5,479,818 A 1/1996 Walter et al.
5,482,049 A 1/1996 Addiss et al.
5,487,760 A 1/1996 Villafana
5,493,738 A 2/1996 Sanderson et al.
5,494,036 A 2/1996 Uber, III et al.
5,494,193 A 2/1996 Kirschner et al.
5,504,474 A 4/1996 Libman et al.
5,505,916 A 4/1996 Berry, Jr.
5,507,412 A 4/1996 Ebert et al.
5,507,737 A 4/1996 Palmskog et al.
5,507,785 A 4/1996 Deno
5,509,888 A 4/1996 Miller
5,509,891 A 4/1996 DeRidder
5,513,945 A 5/1996 Hartmann et al.
5,514,103 A 5/1996 Srisathapat et al.
5,518,504 A 5/1996 Polyak
5,520,606 A 5/1996 Schoolman et al.
5,523,740 A 6/1996 Burgmann et al.
5,534,018 A 7/1996 Wahlstrand et al.
5,535,752 A 7/1996 Halperin et al.
5,538,005 A 7/1996 Harrison et al.
5,541,857 A 7/1996 Walter et al.
5,545,140 A 8/1996 Conero et al.
5,545,151 A 8/1996 O'Connor et al.
5,545,186 A 8/1996 Olson et al.
5,545,214 A 8/1996 Stevens
5,547,470 A 8/1996 Johnson et al.
5,551,427 A 9/1996 Altman
5,551,439 A 9/1996 Hickey
5,554,185 A 9/1996 Block et al.
5,558,644 A 9/1996 Boyd et al.
5,564,434 A 10/1996 Halperin et al.
5,575,770 A 11/1996 Melsky et al.
5,584,803 A 12/1996 Stevens et al.
5,586,629 A 12/1996 Shoberg et al.
5,593,430 A 1/1997 Renger
5,594,665 A 1/1997 Walter et al.
5,596,986 A 1/1997 Goldfarb
5,597,284 A 1/1997 Weltlich et al.
5,610,083 A 3/1997 Chan et al.
5,611,768 A 3/1997 Tutrone, Jr.
5,612,497 A 3/1997 Walter et al.
5,615,671 A 4/1997 Schoonen et al.
5,619,991 A 4/1997 Sloane
5,625,946 A 5/1997 Wildeson et al.
5,626,623 A 5/1997 Kieval et al.
5,626,630 A 5/1997 Markowitz et al.
5,630,836 A 5/1997 Prem et al.
5,634,255 A 6/1997 Bishop et al.
5,637,083 A 6/1997 Bertrand et al.
5,643,207 A 7/1997 Rise
5,645,116 A 7/1997 McDonald
5,650,766 A 7/1997 Burgmann et al.
5,673,585 A 10/1997 Bishop et al.
5,676,690 A 10/1997 Noren et al.
5,681,285 A 10/1997 Ford et al.
5,686,831 A 11/1997 Vandervalk et al.
5,687,734 A 11/1997 Dempsey et al.
5,693,076 A 12/1997 Kaemmerer
5,702,368 A 12/1997 Stevens et al.
5,702,427 A 12/1997 Ecker et al.
5,702,431 A 12/1997 Wang et al.
5,704,352 A 1/1998 Tremblay et al.
5,715,786 A 2/1998 Seiberth et al.
5,715,837 A 2/1998 Chen
5,720,436 A 2/1998 Buschor et al.
5,730,101 A 3/1998 Aupperle et al.
5,732,710 A 3/1998 Rabinovich et al.
5,733,313 A 3/1998 Barreras, Sr. et al.
5,738,652 A 4/1998 Boyd et al.
5,742,233 A 4/1998 Hoffman et al.
5,743,267 A 4/1998 Nikolic et al.
5,749,369 A 5/1998 Rabinovich et al.
5,749,909 A 5/1998 Schroeppel et al.
5,755,687 A 5/1998 Donlon
5,755,748 A 5/1998 Borza et al.
5,765,568 A 6/1998 Sweezer, Jr. et al.
5,769,812 A 6/1998 Stevens et al.
5,771,903 A 6/1998 Jakobsson
5,782,774 A 7/1998 Shmulewitz
5,787,520 A 8/1998 Dunbar
5,791,344 A 8/1998 Schulman et al.
5,792,094 A 8/1998 Stevens et al.
5,792,179 A 8/1998 Sideris
5,795,325 A 8/1998 Valley et al.
5,796,827 A 8/1998 Coppersmith et al.
5,800,375 A 9/1998 Sweezer et al.
5,807,265 A 9/1998 Itoigawa et al.
5,807,336 A 9/1998 Russo et al.
5,810,015 A 9/1998 Flaherty
5,810,757 A 9/1998 Sweezer, Jr. et al.
5,814,016 A 9/1998 Valley et al.
5,817,093 A 10/1998 Williamson, IV et al.
5,833,603 A 11/1998 Kovacs et al.
5,836,300 A 11/1998 Mault
5,836,886 A 11/1998 Itoigawa et al.
5,840,081 A 11/1998 Andersen et al.
5,849,225 A 12/1998 Ebina et al.
5,855,597 A 1/1999 Jayaraman et al.
5,855,601 A 1/1999 Bessler et al.
5,860,938 A 1/1999 Lafontaine et al.
5,861,018 A 1/1999 Feierbach
5,863,366 A 1/1999 Snow
5,868,702 A 2/1999 Stevens et al.
5,873,837 A 2/1999 Lieber et al.
5,875,953 A 3/1999 Shioya et al.
5,879,499 A 3/1999 Corvi
5,881,919 A 3/1999 Womac et al.
5,885,238 A 3/1999 Stevens et al.
5,887,475 A 3/1999 Muldner
5,899,927 A 5/1999 Ecker et al.
5,916,179 A 6/1999 Sharrock
5,916,237 A 6/1999 Schu
5,935,078 A 8/1999 Feierbach
5,938,669 A 8/1999 Klaiber et al.
5,951,487 A 9/1999 Brehmeier-Flick et al.
5,957,861 A 9/1999 Combs et al.
5,967,986 A 10/1999 Cimochowski et al.
5,971,934 A 10/1999 Scherer et al.
5,974,873 A 11/1999 Nelson et al.
5,978,985 A 11/1999 Thurman
5,995,874 A 11/1999 Borza et al.
6,015,386 A 1/2000 Kensey et al.
6,015,387 A 1/2000 Schwartz et al.
6,019,729 A 2/2000 Itoigawa et al.
6,024,704 A 2/2000 Meador et al.
6,030,413 A 2/2000 Lazarus
6,035,461 A 3/2000 Nguyen
6,053,873 A 4/2000 Govari et al.
6,056,723 A 5/2000 Donlon
6,058,330 A 5/2000 Borza et al.
6,059,757 A 5/2000 Macoviak et al.
6,067,474 A 5/2000 Schulman et al.
6,067,991 A 5/2000 Forsell et al.
6,076,016 A 6/2000 Feierbach
6,083,174 A 7/2000 Brehmeier-Flick et al.
6,090,096 A 7/2000 St. Goar et al.

6,102,678 A 8/2000 Peclat et al.
6,102,856 A 8/2000 Groff et al.
6,102,922 A 8/2000 Jakobsson et al.
6,106,477 A 8/2000 Miesel et al.
6,106,551 A 8/2000 Crossett et al.
6,110,145 A 8/2000 Macoviak
6,113,553 A 9/2000 Chubbuck
6,131,664 A 10/2000 Sonnier
6,135,945 A 10/2000 Sultan
6,159,156 A 12/2000 Van Bockel et al.
6,162,180 A 12/2000 Miesel et al.
6,162,245 A 12/2000 Jayaraman et al.
6,168,614 B1 1/2001 Andersen et al.
6,234,745 B1 5/2001 Pugh et al.
6,240,316 B1 5/2001 Richmond et al.
6,240,318 B1 5/2001 Phillips
6,245,102 B1 6/2001 Jayaraman
6,248,080 B1 6/2001 Miesel et al.
6,251,093 B1 6/2001 Valley et al.
6,269,819 B1 8/2001 Oz et al.
6,277,078 B1 8/2001 Porat et al.
6,292,697 B1 9/2001 Roberts
6,309,350 B1 10/2001 VanTassel et al.
6,315,769 B1 11/2001 Peer et al.
6,319,208 B1 11/2001 Abita et al.
6,328,699 B1 12/2001 Eigler et al.
6,338,735 B1 1/2002 Stevens
6,357,438 B1 3/2002 Hansen
6,360,122 B1 3/2002 Fischell et al.
6,360,822 B1 3/2002 Robertson et al.
6,366,817 B1 4/2002 Kung
6,379,308 B1 4/2002 Brockway et al.
6,379,380 B1 4/2002 Satz
6,398,752 B1 6/2002 Sweezer, Jr. et al.
6,409,674 B1 6/2002 Brockway et al.
6,423,031 B1 7/2002 Donlon
6,430,444 B1 8/2002 Borza et al.
6,431,175 B1 8/2002 Penner et al.
6,432,040 B1 8/2002 Meah
6,443,887 B1 9/2002 Derus et al.
6,443,893 B1 9/2002 Schnakenberg et al.
6,450,173 B1 9/2002 Forsell et al.
6,450,946 B1 9/2002 Forsell et al.
6,453,907 B1 9/2002 Forsell et al.
6,454,698 B1 9/2002 Forsell et al.
6,454,699 B1 9/2002 Forsell et al.
6,454,700 B1 9/2002 Forsell et al.
6,454,701 B1 9/2002 Forsell et al.
6,461,292 B1 10/2002 Forsell et al.
6,461,293 B1 10/2002 Forsell et al.
6,463,329 B1 10/2002 Goedeke
6,463,935 B1 10/2002 Forsell et al.
6,464,628 B1 10/2002 Forsell et al.
6,470,212 B1 10/2002 Weijand et al.
6,470,892 B1 10/2002 Forsell et al.
6,471,635 B1 10/2002 Forsell et al.
6,475,136 B1 11/2002 Forsell et al.
6,475,170 B1 11/2002 Doron et al.
6,482,145 B1 11/2002 Forsell et al.
6,482,171 B1 11/2002 Corvi et al.
6,482,177 B1 11/2002 Leinders et al.
6,486,588 B2 11/2002 Doron et al.
6,503,189 B1 1/2003 Forsell et al.
6,504,286 B1 1/2003 Porat et al.
6,531,739 B2 3/2003 Cable et al.
6,533,719 B2 3/2003 Kuyava et al.
6,533,733 B1 3/2003 Ericson et al.
6,542,350 B1 4/2003 Rogers
6,558,321 B1 5/2003 Burd et al.
6,558,994 B2 5/2003 Cha et al.
6,573,563 B2 6/2003 Lee et al.
6,582,462 B1 6/2003 Andersen et al.
6,599,250 B2 7/2003 Webb et al.
6,605,112 B1 8/2003 Moll et al.
6,629,534 B1 10/2003 St. Goar et al.
6,640,137 B2 10/2003 MacDonald
6,641,610 B2 11/2003 Wolf et al.
6,645,143 B2 11/2003 VanTassel et al.
6,673,109 B2 1/2004 Cox
6,678,561 B2 1/2004 Forsell et al.
6,682,480 B1 1/2004 Habib et al.
6,682,503 B1 1/2004 Fariss et al.
6,682,559 B2 1/2004 Myers et al.
6,695,866 B1 2/2004 Kuehn et al.
6,709,385 B2 3/2004 Forsell et al.
6,718,200 B2 4/2004 Marmaropoulos et al.
6,719,787 B2 4/2004 Cox
6,719,788 B2 4/2004 Cox
6,719,789 B2 4/2004 Cox
6,731,976 B2 5/2004 Penn et al.
6,733,525 B2 5/2004 Yang et al.
6,736,846 B2 5/2004 Cox
6,752,813 B2 6/2004 Goldfarb et al.
6,796,942 B1 9/2004 Kreiner et al.
6,822,343 B2 11/2004 Estevez
6,851,628 B1 2/2005 Garrison et al.
6,855,115 B2 2/2005 Fonseca et al.
6,889,772 B2 5/2005 Buytaert et al.
6,890,300 B2 5/2005 Lloyd et al.
6,896,651 B2 5/2005 Gross et al.
6,896,690 B1 5/2005 Lambrecht et al.
6,913,600 B2 7/2005 Valley et al.
6,915,165 B2 7/2005 Forsell et al.
6,926,246 B2 8/2005 Ginggen et al.
6,929,653 B2 8/2005 Strecter
6,932,792 B1 8/2005 St. Goar et al.
6,951,229 B2 10/2005 Garrison et al.
6,951,571 B1 10/2005 Srivastava
6,953,429 B2 10/2005 Forsell et al.
6,961,619 B2 11/2005 Casey
6,970,742 B2 11/2005 Mann et al.
6,979,350 B2 12/2005 Moll et al.
6,985,078 B2 1/2006 Suzuki et al.
6,989,027 B2 1/2006 Allen et al.
7,011,095 B2 3/2006 Wolf et al.
7,011,624 B2 3/2006 Forsell et al.
7,017,583 B2 3/2006 Forsell et al.
7,018,406 B2 3/2006 Seguin et al.
7,021,402 B2 4/2006 Beato et al.
7,025,727 B2 4/2006 Brockway et al.
7,044,920 B2 5/2006 Letort et al.
7,060,080 B2 6/2006 Bachmann et al.
7,081,683 B2 7/2006 Ariav et al.
7,109,933 B2 9/2006 Ito et al.
7,131,447 B2 11/2006 Sterman et al.
7,131,945 B2 11/2006 Fink et al.
7,134,580 B2 11/2006 Garrison et al.
7,144,400 B2 12/2006 Byrum et al.
7,147,640 B2 12/2006 Huebner et al.
7,153,262 B2 12/2006 Stivoric et al.
7,187,978 B2 3/2007 Malek et al.
7,225,032 B2 5/2007 Schmeling et al.
7,257,438 B2 8/2007 Kinast
7,285,090 B2 10/2007 Stivoric et al.
2001/0011543 A1 8/2001 Forsell
2001/0041823 A1 11/2001 Snyder et al.
2002/0049394 A1 4/2002 Roy et al.
2002/0120200 A1 8/2002 Brockway et al.
2002/0138009 A1 9/2002 Brockway et al.
2002/0177782 A1 11/2002 Penner
2003/0009201 A1 1/2003 Forsell
2003/0030893 A1 2/2003 Cornelius et al.
2003/0032857 A1 2/2003 Forsell
2003/0037591 A1 2/2003 Ashton et al.
2003/0045775 A1 3/2003 Forsell
2003/0066536 A1 4/2003 Forsell 2003/0088148 A1 5/2003 Forsell
2003/0092962 A1 5/2003 Forsell
2003/0093117 A1 5/2003 Saadat
2003/0100929 A1 5/2003 Forsell
2003/0105385 A1 6/2003 Forsell
2003/0109771 A1 6/2003 Forsell
2003/0114729 A1 6/2003 Forsell
2003/0125605 A1 7/2003 Forsell
2003/0125768 A1 7/2003 Peter
2003/0135089 A1 7/2003 Forsell
2003/0135090 A1 7/2003 Forsell
2003/0136417 A1 7/2003 Fonseca et al.
2003/0144648 A1 7/2003 Forsell
2003/0163079 A1 8/2003 Burnett
2003/0216666 A1 11/2003 Ericson et al.
2004/0021322 A1 2/2004 Ariav
2004/0054352 A1 3/2004 Adams et al.
2004/0113790 A1 6/2004 Hamel et al.
2004/0133092 A1 7/2004 Kain
2004/0147969 A1 7/2004 Mann et al.
2004/0172087 A1 9/2004 Forsell
2004/0186396 A1 9/2004 Roy et al.
2004/0254537 A1 12/2004 Conlon et al.
2005/0015014 A1 1/2005 Fonseca et al.
2005/0025979 A1 2/2005 Sandt et al.
2005/0027175 A1 2/2005 Yang
2005/0038328 A1 2/2005 Stoehrer et al.
2005/0061079 A1 3/2005 Schulman
2005/0102026 A1 5/2005 Turner et al.
2005/0159789 A1 7/2005 Brockway et al.
2005/0165317 A1 7/2005 Turner et al.
2005/0182330 A1 8/2005 Brockway et al.
2005/0187482 A1 8/2005 O'Brien et al.
2005/0187488 A1 8/2005 Wolf
2005/0192642 A1 9/2005 Forsell
2005/0240155 A1 10/2005 Conlon
2005/0240156 A1 10/2005 Conlon
2005/0250979 A1 11/2005 Coe
2005/0256549 A1 11/2005 Holzer
2005/0267406 A1 12/2005 Hassler
2005/0267500 A1 12/2005 Hassler et al.
2005/0272968 A1 12/2005 Byrum et al.
2005/0277960 A1 12/2005 Hassler et al.
2005/0277974 A1 12/2005 Hassler et al.
2005/0288604 A1 12/2005 Eigler et al.
2005/0288720 A1 12/2005 Ross et al.
2005/0288721 A1 12/2005 Girouard et al.
2005/0288739 A1 12/2005 Hassler et al.
2005/0288740 A1 12/2005 Hassler et al.
2005/0288741 A1 12/2005 Hassler et al.
2005/0288742 A1 12/2005 Giordano et al.
2006/0002035 A1 1/2006 Gao et al.
2006/0010090 A1 1/2006 Brockway et al.
2006/0020224 A1 1/2006 Geiger
2006/0020305 A1 1/2006 Desai et al.
2006/0035446 A1 2/2006 Chang et al.
2006/0047205 A1 3/2006 Ludomirsky et al.
2006/0049714 A1 3/2006 Liu et al.
2006/0058627 A1 3/2006 Flaherty et al.
2006/0064134 A1 3/2006 Mazar et al.
2006/0085051 A1 4/2006 Fritsch
2006/0089571 A1 4/2006 Gertner
2006/0094966 A1 5/2006 Brockway et al.
2006/0100531 A1 5/2006 Moser
2006/0113187 A1 6/2006 Deng et al.
2006/0122285 A1 6/2006 Falloon et al.
2006/0122863 A1 6/2006 Gottesman et al.
2006/0142635 A1 6/2006 Forsell
2006/0149124 A1 7/2006 Forsell
2006/0149324 A1 7/2006 Mann et al.
2006/0149327 A1 7/2006 Hedberg et al.
2006/0157701 A1 7/2006 Bauer et al.
2006/0161186 A1 7/2006 Hassler et al.
2006/0178617 A1 8/2006 Adams et al.
2006/0178695 A1 8/2006 Decant et al.
2006/0183967 A1 8/2006 Lechner
2006/0184206 A1 8/2006 Baker et al.
2006/0189887 A1 8/2006 Hassler et al.
2006/0189888 A1 8/2006 Hassler et al.
2006/0189889 A1 8/2006 Gertner
2006/0199997 A1 9/2006 Hassler et al.
2006/0211912 A1 9/2006 Dlugos et al.
2006/0211913 A1 9/2006 Dlugos et al.
2006/0211914 A1 9/2006 Hassler et al.
2006/0217668 A1 9/2006 Schulze et al.
2006/0217673 A1 9/2006 Schulze et al.
2006/0235310 A1 10/2006 O'Brien et al.
2006/0235439 A1 10/2006 Molitor et al.
2006/0235448 A1 10/2006 Roslin et al.
2006/0244914 A1 11/2006 Cech et al.
2006/0247682 A1 11/2006 Gerber et al.
2006/0247719 A1 11/2006 Maschino et al.
2006/0247722 A1 11/2006 Maschino et al.
2006/0247723 A1 11/2006 Gerber et al.
2006/0247724 A1 11/2006 Gerber et al.
2006/0247725 A1 11/2006 Gerber et al.
2006/0252982 A1 11/2006 Hassler et al.
2006/0293625 A1 12/2006 Hunt et al.
2006/0293626 A1 12/2006 Byrum et al.
2006/0293627 A1 12/2006 Byrum et al.
2007/0010790 A1 1/2007 Byrum et al.
2007/0027356 A1 2/2007 Ortiz
2007/0027493 A1 2/2007 Ben-Haim et al.
2007/0067206 A1 3/2007 Haggerty et al.
2007/0070906 A1 3/2007 Thakur
2007/0072452 A1 3/2007 Inagaki et al.
2007/0081304 A1 4/2007 Takeguchi
2007/0156013 A1 7/2007 Birk
2007/0167672 A1 7/2007 Dlugos et al.
2007/0173881 A1 7/2007 Birk et al.
2007/0179583 A1 8/2007 Goetzinger et al.
2007/0185374 A1 8/2007 Kick et al.
2007/0208313 A1 9/2007 Conlon et al.
2007/0225781 A1 9/2007 Saadat et al.
2008/0009680 A1 1/2008 Hassler

FOREIGN PATENT DOCUMENTS

CA 1119469 3/1982
CA 1275135 10/1990
CA 1277885 12/1990
CA 1317482 5/1993
CA 2082015 5/1993
CA 1327191 2/1994
CA 2119101 9/1994
CA 2305998 4/1999
CN 1059035 2/1992
CN 1119469 3/1996
CN 1241003 1/2000
EA 4581 6/2004
EP 125387 B1 11/1984
EP 417171 3/1991
EP 508141 10/1992
EP 568730 11/1993
EP 605302 7/1994
EP 660482 6/1995
EP 714017 5/1996
EP 769340 4/1997
EP 846475 6/1998
EP 848780 6/1998
EP 876808 11/1998
EP 888079 1/1999
EP 914059 5/1999
EP 981293 3/2000
EP 997680 5/2000
EP 1003021 5/2000

| EP | 1022983 | 8/2000 |
|---|---|---|
| EP | 1050265 | 11/2000 |
| EP | 1115329 | 7/2001 |
| EP | 1119314 | 8/2001 |
| EP | 1128871 | 9/2001 |
| EP | 1202674 | 5/2002 |
| EP | 1213991 | 6/2002 |
| EP | 1253877 | 11/2002 |
| EP | 1253879 | 11/2002 |
| EP | 1253880 | 11/2002 |
| EP | 1253881 | 11/2002 |
| EP | 1253883 | 11/2002 |
| EP | 1253888 | 11/2002 |
| EP | 1255511 | 11/2002 |
| EP | 1255513 | 11/2002 |
| EP | 1255514 | 11/2002 |
| EP | 1263355 | 12/2002 |
| EP | 1263357 | 12/2002 |
| EP | 1284691 | 2/2003 |
| EP | 1374758 | 1/2004 |
| EP | 1488735 | 12/2004 |
| EP | 1500411 | 1/2005 |
| EP | 1510306 | 3/2005 |
| EP | 1518514 | 3/2005 |
| EP | 1545303 | 6/2005 |
| EP | 1547549 | 6/2005 |
| EP | 1563814 | 8/2005 |
| EP | 1568338 | 8/2005 |
| EP | 1582175 | 10/2005 |
| EP | 1582176 | 10/2005 |
| EP | 1584303 | 10/2005 |
| EP | 1586283 | 10/2005 |
| EP | 1591086 | 11/2005 |
| EP | 1593359 | 11/2005 |
| EP | 1598030 | 11/2005 |
| EP | 1609440 | 12/2005 |
| EP | 1674033 | 6/2006 |
| EP | 1736123 | 12/2006 |
| EP | 1799119 | 6/2007 |
| EP | 1832254 A1 | 9/2007 |
| GB | 2355937 | 5/2001 |
| WO | WO-8911244 | 11/1989 |
| WO | WO-8911701 | 11/1989 |
| WO | WO-9004368 | 5/1990 |
| WO | WO-9511057 | 4/1995 |
| WO | WO-9715351 | 5/1997 |
| WO | WO-9733513 | 9/1997 |
| WO | WO-9833554 | 8/1998 |
| WO | WO-9835610 | 8/1998 |
| WO | WO-9901063 | 1/1999 |
| WO | WO-9918850 | 4/1999 |
| WO | WO-0004945 | 2/2000 |
| WO | WO-0033738 | 6/2000 |
| WO | WO-0072899 | 12/2000 |
| WO | WO-0104487 | 1/2001 |
| WO | WO-0112075 | 2/2001 |
| WO | WO-0112076 | 2/2001 |
| WO | WO-0112077 | 2/2001 |
| WO | WO-0112078 | 2/2001 |
| WO | WO-0121066 | 3/2001 |
| WO | WO-0136014 | 5/2001 |
| WO | WO-0145485 | 6/2001 |
| WO | WO-0145486 | 6/2001 |
| WO | WO-0147431 | 7/2001 |
| WO | WO-0147432 | 7/2001 |
| WO | WO-0147433 | 7/2001 |
| WO | WO-0147434 | 7/2001 |
| WO | WO-0147435 | 7/2001 |
| WO | WO-0147440 | 7/2001 |
| WO | WO-0147575 | 7/2001 |
| WO | WO-0148451 | 7/2001 |
| WO | WO-0149245 | 7/2001 |
| WO | WO-0150832 | 7/2001 |
| WO | WO-0150833 | 7/2001 |
| WO | WO-0154626 | 8/2001 |
| WO | WO-0158388 | 8/2001 |
| WO | WO-0158390 | 8/2001 |
| WO | WO-0158391 | 8/2001 |
| WO | WO-0158393 | 8/2001 |
| WO | WO-0160453 | 8/2001 |
| WO | WO-0181890 | 11/2001 |
| WO | WO-0200118 | 1/2002 |
| WO | WO-0215769 | 2/2002 |
| WO | WO-0226161 | 4/2002 |
| WO | WO-02053228 | 7/2002 |
| WO | WO-02055126 | 7/2002 |
| WO | WO-02058551 | 8/2002 |
| WO | WO-02065894 | 8/2002 |
| WO | WO-02076289 | 10/2002 |
| WO | WO-02082984 | 10/2002 |
| WO | WO-02089655 | 11/2002 |
| WO | WO-02090894 | 11/2002 |
| WO | WO-02100481 | 12/2002 |
| WO | WO-03002192 | 1/2003 |
| WO | WO-03002193 | 1/2003 |
| WO | WO-03020182 | 3/2003 |
| WO | WO-03061467 | 7/2003 |
| WO | WO-03061504 | 7/2003 |
| WO | WO-03096889 | 11/2003 |
| WO | WO-2004014456 | 2/2004 |
| WO | WO-2004019773 | 3/2004 |
| WO | WO-2004058101 | 7/2004 |
| WO | WO-2004066879 | 8/2004 |
| WO | WO-2004110263 | 12/2004 |
| WO | WO-2005000206 | 1/2005 |
| WO | WO-2005007075 | 1/2005 |
| WO | 05044369 A1 | 5/2005 |
| WO | WO-2005107583 | 11/2005 |
| WO | WO-2006001851 | 1/2006 |
| WO | WO-2006035446 | 4/2006 |
| WO | WO-2006113187 | 10/2006 |
| WO | WO-2006122285 | 11/2006 |
| WO | WO-2007067206 | 6/2007 |
| WO | WO-2007070906 | 6/2007 |
| WO | WO-2007072452 | 6/2007 |
| WO | WO-2007081304 | 7/2007 |
| WO | WO-2007104356 | 9/2007 |

OTHER PUBLICATIONS

"Rad Hard Aerospace Components Products", Honeywell product and service information from website http://www.honeywell.com/sites/portal?smap=aerospace&page=Radiation-Hardened-Electronics3&theme=T6&catID=C815147E4-8786-29FE-49EB-C21C8790AA99&id=H0166BA51-5344-E57E-5C37-C6333EA43F61&sel=1; 1 page.

"Radiation Hardened Electronics and Radiation Technology", Honeywell product and service information from website http://www.honeywell.com/sites/portal?smap=aerospace&page=Radiation-Hardened-Electronics&theme=T4; 2 pages.

Kirchner, G., "Honeywell and Synopsys: Concept-to-Parts Solutions for Next Generation Rad-Hard ASICs", in online magazine Compiler, http://www.synopsys.com/news/pubs/compiler/artlead_redasic-apr05.html, Apr. 2005, 5 pages.

P.A. Neukomm and H. Kundig, "Passive Wireless Actuator Control and Sensor Signal Transmission," Sensors and Actuators, A21-A23 (1990) 258-262.

Eurpoean Search Report mailed Apr. 24, 2009 in EP Application No. 09250304.4.

Eurpoean Search Report mailed Jun. 9, 2009 in EP Application No. 09250306.9.

European Patent Search Report, Application No. EP09250301, issued Jun. 4, 2009, 2 pp.

POWERING IMPLANTABLE RESTRICTION SYSTEMS USING LIGHT

FIELD OF THE INVENTION

The present invention relates to methods and devices for providing power to implantable restriction systems.

BACKGROUND OF THE INVENTION

Obesity is becoming a growing concern, particularly in the United States, as the number of obese people continues to increase, and more is learned about the negative health effects of obesity. Morbid obesity, in which a person is 100 pounds or more over ideal body weight, in particular poses significant risks for severe health problems. Accordingly, a great deal of attention is being focused on treating obese patients. One method of treating morbid obesity has been to place a restriction device, such as an elongated band, about the upper portion of the stomach. Gastric bands have typically comprised a fluid-filled elastomeric balloon with fixed endpoints that encircles the stomach just inferior to the esophageal-gastric junction to form a small gastric pouch above the band and a reduced stoma opening in the stomach. When fluid is infused into the balloon, the band expands against the stomach creating a food intake restriction or stoma in the stomach. To decrease this restriction, fluid is removed from the band. The effect of the band is to reduce the available stomach volume and thus the amount of food that can be consumed before becoming "full."

Food restriction devices have also comprised mechanically adjusted bands that similarly encircle the upper portion of the stomach. These bands include any number of resilient materials or gearing devices, as well as drive members, for adjusting the bands. Additionally, gastric bands have been developed that include both hydraulic and mechanical drive elements. It is also known to restrict the available food volume in the stomach cavity by implanting an inflatable elastomeric balloon within the stomach cavity itself. The balloon is filled with a fluid to expand against the stomach walls and, thereby, decrease the available food volume within the stomach.

With each of the above-described food restriction devices, safe, effective treatment requires that the device be regularly monitored and adjusted to vary the degree of restriction applied to the stomach. Traditionally, adjusting a gastric band required a scheduled clinician visit during which a Huber needle and syringe were used to penetrate the patient's skin and add or remove fluid from the balloon via the injection port. More recently, implantable pumps have been developed which enable non-invasive adjustments of the band. An external programmer communicates with the implanted pump using telemetry to control the pump. During a scheduled visit, a physician places a hand-held portion of the programmer near the gastric implant and transmits command signals to the implant. The implant in turn adjusts the band and transmits a response command to the programmer.

Implants such as those described above include electronics which require a power source that is sufficient for the intended function, such as making adjustments to the gastric band. Such devices may be internally powered by a battery or capacitor while others may be powered by an externally coupled power source or passive telemetry system. When coupling externally, the efficiencies between the implant and external device diminish substantially as the distance between them increases. There can also be significant power losses through tissue.

Accordingly, there is a need for methods and devices for charging implanted electronics efficiently through tissue by using external and/or non-invasive techniques. It would also be advantageous for a patient to be able to recharge implants without having to travel to a scheduled clinician visit.

SUMMARY OF THE INVENTION

The present invention provides methods and devices for providing power to an implantable restriction system. In one exemplary embodiment, a system for forming a restriction in a patient is provided and includes an implantable restriction device adapted to form a restriction in a pathway within a patient. For example, the implantable restriction device can include a gastric band and a housing in communication with the gastric band. The implantable restriction device can also include a communicating member that powers the implantable restriction device. The system can further include an external apparatus that is operable to communicate with the communicating member by sending power and/or data signals to the communicating member and/or by receiving data signals from the communicating member. The communicating member can also be configured to send data signals to an external device. The external apparatus can optionally include a gauge that is effective to indicate whether the external apparatus is effectively communicating with the communicating member.

In one embodiment, the communicating member can be adapted to convert light waves into energy, and the external apparatus can be an energy transfer apparatus having a light source that is operable to communicate light to the communicating member. The energy transfer apparatus can include a gauge effective to indicate whether the light waves are being communicated between the light source and the communicating member effective to power the implantable restriction device or communicate data. In an embodiment, the communicating member can be a photovoltaic cell array, a silicon nanowire bundle, or a crystalline silicon cell array, and the light source can emit infrared light waves in a range of about 0.70.mu.m to 1,000.mu.m. Alternatively, the light source can emit visible light waves in a range of about 400 nm to 1,000 nm or ultraviolet light waves in a range of about 280 nm to 400 nm.

In another embodiment, the communicating member can be adapted to utilize a temperature differential to power the implantable restriction device, the energy transfer apparatus can have a temperature source operable to create a temperature differential across the communicating member to power the implantable restriction device. In an exemplary embodiment, the communicating member is a thermogenerator. The temperature source can be, for example, ice, a thermoelectric cooler, a heating source, and a blood vessel. The communicating member can be configured to utilize a temperature differential between the temperature source and an anatomical reference temperature to produce energy to power the implantable restriction device. In another embodiment, the gauge can be effective to indicate whether a temperature differential exists between the temperature source and the communicating member effective to power the implantable restriction device.

In another embodiment, the communicating member can have a kinetic motion apparatus operable to convert motion into energy to power the implantable restriction device. The kinetic motion apparatus can include a housing, a magnet disposed within the housing, and a wire coil disposed around the housing. The wire coil can be in electrical communication with the implantable restriction device and the magnet can be configured to move relative to the wire coil to create electrical energy to power the implantable restriction device. The kinetic motion apparatus can further include a storage device for storing the electrical energy produced from movement of the magnet. The system may also include an external device that may include a driver adapted to produce corresponding oscillations, vibrations, or other motions in the kinetic motion apparatus effective to power the implantable restriction device. Alternatively, an external oscillating electromagnet can induce sympathetic oscillations in the magnet disposed within the housing. In another embodiment, the gauge can be adapted to indicate a charge status of the implantable restriction device.

In a further exemplary embodiment, a kinetic motion apparatus can include a counterweight coupled to a drive gear and configured to rotate freely about a pivot point when the kinetic motion apparatus is rotated in response to patient movement. The kinetic motion apparatus can also include an electric generator configured to receive mechanical energy from the drive gear and convert it to electrical energy to power the implantable restriction device.

In one embodiment, a kinetic motion apparatus can include a piezoelectric device configured to convert internal muscle and/or organ movement within a patient into electrical energy to power the implantable restriction device. The piezoelectric device can also be configured to convert digestive movement of a patient's stomach against the gastric band into electrical energy to power the implantable restriction device.

Methods are also provided for powering an implantable restriction device. In one embodiment, the method can include activating a light source to transfer light through tissue to a communicating member disposed within an implantable restriction device. The communicating member can convert the light to electrical current to power the implantable restriction device. The light source can be on an external device, and the method can further include positioning the external device adjacent to a skin surface and in proximity to the communicating member implanted within tissue. The external device can also optionally include a gauge that indicates whether light transferred between the light source and the communicating member is effective to power the implantable restriction device. Additionally, the external device can receive data from the communicating member which includes at least one measurement of pressure of fluid within the implantable restriction device. In an exemplary embodiment, the light source emits infrared light with a wavelength in a range of about 0.70 μm to 1,000 μm. Alternatively, the light source emits visible light with a wavelength in a range of about 400 nm to 750 nm or ultraviolet light with a wavelength in the range of about 280 nm to 400 nm.

In another embodiment, a method is provided for powering an implantable restriction device and includes placing a temperature source on a tissue surface adjacent to a communicating member disposed within an implantable restriction device implanted in a patient. The communicating member utilizes a temperature differential to power the implantable restriction device. The communicating member may be placed close to the skin such that it resides in a temperature gradient between the external environment and the body core. Alternatively, the thermogenerator can be placed in contact with a large blood vessel since the body uses the blood stream to convey heat to and from the body. Thus, a natural temperature gradient exists in the body with may be used to generate power. The temperature source can be on an external device, and the external device can receive data from the communicating member. The external device can also include a gauge that indicates whether a temperature differential exists between the temperature source and the communicating member effective to power the implantable restriction device. The data can include at least one measurement of pressure of fluid within the implantable restriction device. In one embodiment, the temperature source can be ice, a thermoelectric cooler, and/or a heating source placed on or near a tissue surface adjacent to the thermogenerator creating a temperature differential with an anatomical reference temperature across the thermogenerator to produce electrical current to power the implantable restriction device.

In still another embodiment, a method for providing power to an implantable restriction device is provided and includes driving a communicating member coupled to an implantable restriction device implanted in a patient to power the implantable restriction device, where the communicating member includes a kinetic motion apparatus. The kinetic motion apparatus can include a metal wire and a magnet and the metal wire and a magnetic field created by the magnet move relative to one another, thereby generating electrical energy to power the implantable restriction device. In an exemplary embodiment, the metal wire and the magnetic field move relative to one another in response to motion by the patient. The kinetic motion apparatus can also be driven by an external oscillating electromagnet that induces sympathetic oscillations in the magnet. Alternatively, the kinetic motion apparatus is driven by a vibration element that causes the metal wire to move through the magnetic field. In another embodiment, the communicating member can be in communication with an external device that receives data from the communicating member and which can include a gauge that indicates a charge status of the implantable restriction device. The kinetic motion apparatus can alternatively include a counterweight coupled to a drive gear that rotates freely about a pivot point in response to patient movement. Rotation of the counterweight and drive gear can generate mechanical energy that is converted into electrical energy to power the implantable restriction device. In one exemplary embodiment, the kinetic motion apparatus includes a piezoelectric device that converts internal muscle and/or organ movement within a patient into energy to power the implantable restriction device. The piezoelectric device can also convert digestive motion of the stomach against the gastric band into electrical energy to power the implantable restriction device. The method can include storing excess energy generated by the kinetic motion apparatus in a storage device.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
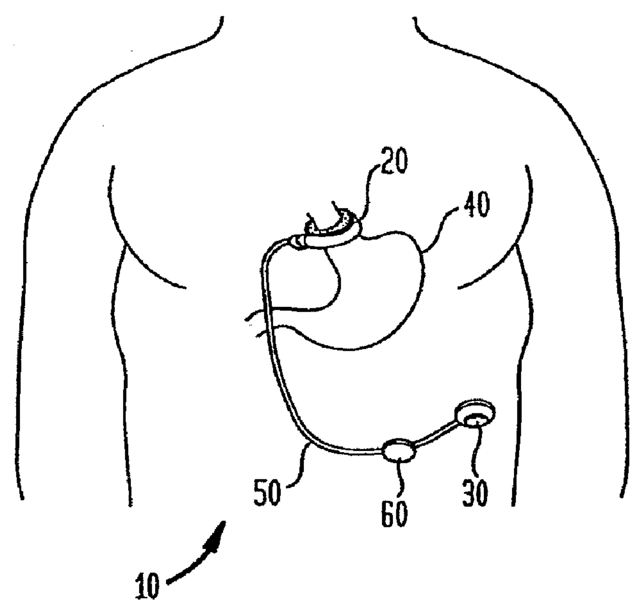
FIG. 1 is a representation of a food intake restriction system implanted in a patient to form a restriction in the patient's stomach.

Various powering devices are provided for transferring energy from an external source through tissue to a communicating member implanted in a patient. The energy transferred to the communicating member can be used to provide power to an implantable restriction device that is implanted to form a restriction in a pathway within a patient. While the present invention disclosed herein can be used with a variety of implantable restriction devices known in the art, FIG. 1 illustrates one exemplary embodiment of a food intake restriction system 10. As shown, the system 10 generally includes an adjustable gastric band 20 that is configured to be positioned around the upper portion of a patient's stomach 40. In addition, the system 10 can include a communicating member capable of providing power to various devices configured to perform any number of tasks within the system 10, as will be described below.

The communicating member can be located anywhere in the system 10. For example, in one embodiment, the communicating member can be disposed within an injection port 30 shown in FIG. 1. The injection port 30 can be in fluid communication with the gastric band for allowing fluid to be introduced into and removed from the band to alter the amount of restriction provided by the band. Alternatively, or in addition, the communicating member can be disposed within a housing 60 that can house various components. In the illustrated embodiment, the system 10 includes both an injection port 30 and a housing 60. Both the injection port 30 and the housing 60 are coupled to the adjustable gastric band 20, e.g., via a catheter 50. A person skilled in the art will appreciate that the system need not include an injection port and/or housing, and that the communicating member can be positioned anywhere along the system 10.

In an exemplary embodiment, the communicating member can convert energy received from an external source to provide power to devices within the system 10 that measure and/or monitor various conditions of the system 10, that make adjustments to the gastric band 20 and/or other aspects of the system 10, and/or that measure/monitor various physiological parameters. Such devices can include, for example, sensors, pumps, bands and/or any other monitoring and/or adjustment devices having circuitry which requires electrical power. The communicating member can be configured to repeatedly receive energy from an external source, convert the energy to electrical power, and store the power in a capacitor, battery or other power storage device known in the art for later use by the device(s) within the system 10. Alternatively, the communicating member can be configured to transfer the converted power directly to the device(s) as needed. In addition, the communicating member can be configured to transmit and receive data to and from an external source. For example, the communicating member can receive command signals from an external source related to powering the system 10. The communicating member can also transmit various anatomical measurements taken within a patient's body to an external device or reader, as well as to transmit information regarding the charge status of the system 10.

The communicating member can take any form known in the art, and various embodiments of the communicating member are provided in detail below. In certain exemplary embodiments, the communicating member can take the form of a sensor capable of receiving energy from an external source for measuring and monitoring various parameters of the system 10; an antenna such as a dipole antenna, a monopole antenna with appropriate counterpoise, or an inductive coil capable of receiving energy through tissue; and/or any other devices known in the art which are capable of aiding in the powering, measuring, monitoring, and/or adjusting of the system 10 and/or other physiological parameters associated with the system 10.

Figure 2:
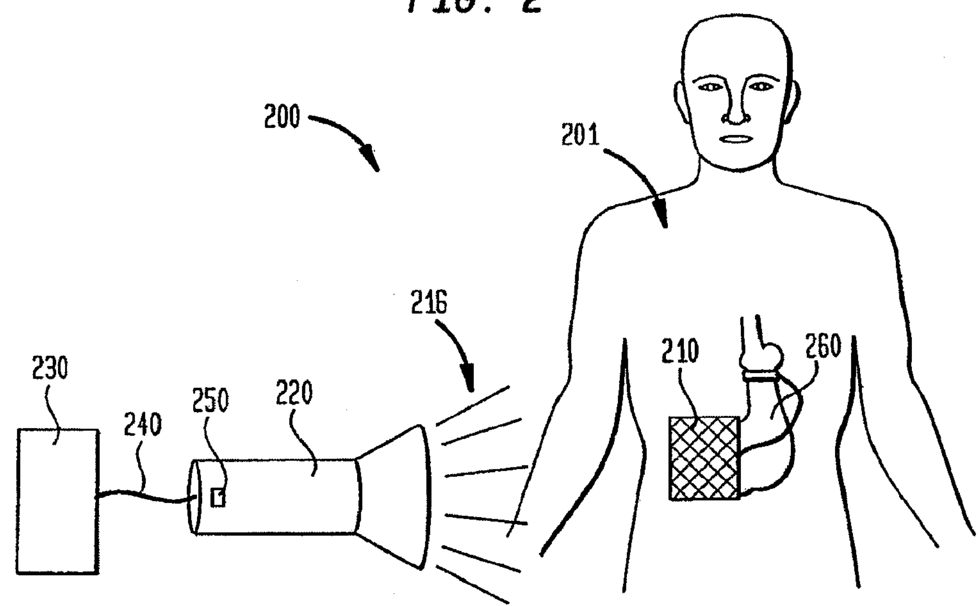
FIG. 2 is a representation of a light powering device for powering the food intake restriction system of FIG. 1.

In one exemplary embodiment shown in FIG. 2, the communicating member is in the form of a photovoltaic cell array or solar cell 210 adapted to receive light waves 216 from an external apparatus 200. The external energy apparatus 200 can include a light source that generates the light waves 216. The light source can be configured in many ways known in the art, but in the illustrated embodiment, it is in the form of a hand-held external device 220 that is electrically connected to a power source 230, such as an electrical outlet or a battery, via an electric cable 240. The external device 220 can also include a switch 250 that enables a user to turn the external device 220 on or off as needed. When the external device 220 is in the "on" position, it can be configured to generate light waves 216 in the infrared range of about 0.70 μm to 1,000 μm. Alternatively or in addition, the external device 220 can be configured to generate light waves 216 in the visible range of about 400 nm to 750 nm or light waves 216 in the ultraviolet range of about 250 nm to 400 nm. Although not shown in FIG. 2, the external device 220 can also include a gauge effective to indicate whether light waves 216 are being communicated between the external device 220 and the solar cell 210 that are effective to power and/or charge the implantable restriction device. The indication given by the gauge can take the form of any notification means known in the art, including a light, such as an LED, an audible noise, and/or a vibration. Alternatively, a silicon nanowire can convert light energy into electric energy on the scale to power low power sensor devices.

In an exemplary embodiment, in use the solar cell 210 can be implanted beneath a tissue surface, e.g., in a patient's abdomen or fascia layer. A user can position the external device 220 in proximity to the implanted solar cell 210 and direct the light waves 216 towards a surface of the solar cell 210 implanted near a surface of a patient's skin. The solar cell 210 can receive and absorb the light waves 216, convert the light waves 216 into electrical power using methods well known in the art, and store them in a device, for example, a capacitor or battery, for later use by the implantable restriction device. Alternatively, the solar cell 210 can immediately transfer the energy via a cable 260 and/or via a wireless transfer to power other devices within the implantable restriction device for monitoring and/or adjusting the gastric band or performing other tasks as described above.

Figure 3:
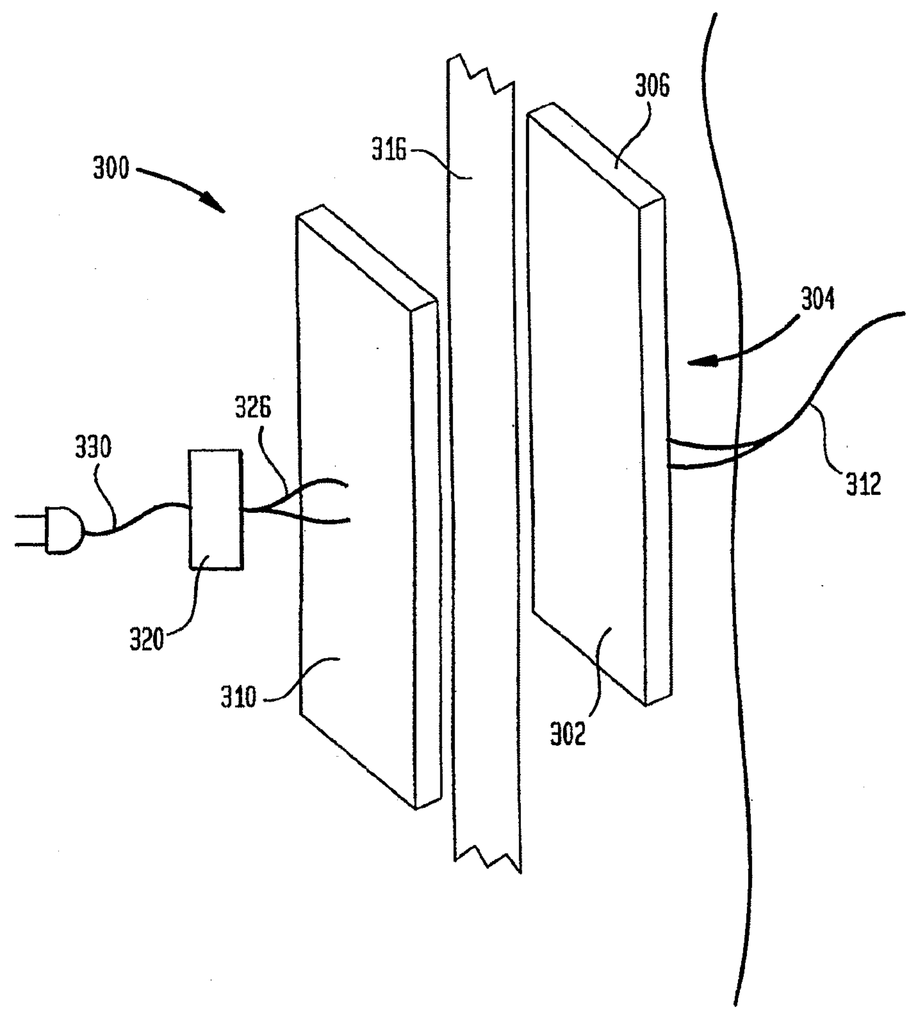
FIG. 3 is representation of a thermoelectric powering device for powering the food intake restriction system of FIG. 1.

In another embodiment shown in FIG. 3, the communicating member can be in the form of a thermoelectric generator

306, such as a Peltier device, configured to use a temperature differential to generate electricity. The external device can include a thermoelectric powering device 300 adapted to power an implantable restriction device implanted within a patient. In an exemplary embodiment, the generator 306 can be implanted under a patient's skin and a temperature differential can be created across the generator 306 by providing an external temperature source which is different than body temperature. As shown, the generator 306 includes a first side 302, which faces outward from the patient's body and is positioned just under the skin. The generator 306 also includes a second side 304 which faces towards an interior of the patient's body. The generator 306 includes electrical leads 312 which can be connected to a storage device, such as a capacitor or battery, or directly to the devices within the implantable restriction device. A means for monitoring the charge level of the storage device may also be included.

As shown in FIG. 3, the thermoelectric powering device includes a temperature source 310. A person skilled in the art will appreciate that the temperature source 310 can be any device or element which is capable of producing a temperature that is different than the temperature associated with the second side 304 of the generator 306. For example, if the temperature of the second side 304 of the generator 306 is at an anatomical reference temperature such as a human body temperature, then the temperature source 310 can be a piece of ice which is at a temperature cooler than the anatomical reference temperature. Alternatively, the first side 302 of the generator 306 can be placed in contact with a large blood vessel within the body, since the body uses the blood stream to convey heat to and from the body. A natural temperature gradient exists in the body between the blood vessel and the body, and therefore between the first side 302 and the second side 304, which can be used to generate power.

In an exemplary embodiment, in use, when a patient or physician places the temperature source 310, e.g. ice, against a tissue surface 316, in proximity to the first side 302 of the implanted generator 306, a temperature differential is created across the generator 306, thereby causing it to generate electricity. A patient and/or physician can place the temperature source 310 against an area of the patient's skin that covers the first side 302 of the implanted generator 306. The temperature source 310 will change the temperature of the first side 302 of the generator so that there is a difference in temperature between the first side 302 and the second side 304 effective to generate electricity. In another example, the temperature source 310 can be a second Peltier device used as a thermoelectric cooler so that one side of the device is much cooler than the temperature of the second side 304 of the implanted generator 306. The thermoelectric cooler can then be placed adjacent to the tissue surface 316 in proximity to the first side 302 of the implanted generator 306, thereby creating a temperature differential across the generator 306 to produce electricity. Alternatively, the temperature source 310 can be eddy-current heating of a conductive component connected to or within the implantable restrictive device. The eddy current may be generated by an inductive coupled external alternating power source. Heating may be controlled for example by the mass of the conductive component, the size and shape of the component, magnetic permeability of the conductive component, resistivity of the conductive component, external power coupling frequency or the external power output level, etc. In one exemplary embodiment, the heat source could be a heating pad placed on or near the tissue surface. The electricity which is generated can then be used by devices within the implantable restriction device as needed.

The temperature source 310 can alternatively be connected to or disposed within an external device 320. The external device 320 can include a gauge that indicates whether a temperature differential exists between the temperature source 310 and the generator 306 that is effective to charge and/or power the implantable restriction device. The indication given by the gauge can take the form of any notification means known in the art, including a light, such as an LED, an audible noise, and/or a vibration. If the temperature source 310 is ice or another temperature element which doesn't require electrical power, an external device 320 may not be required for the purpose of providing power. If the temperature source 310 is a thermoelectric cooler or other electrically powered temperature source as illustrated in FIG. 3, then the external device 320 can provide power to the temperature source 310 via electrical leads 326. The external source 320 can contain batteries or other power source, or can be connected to a wall power source via cable 330.

Figure 4:
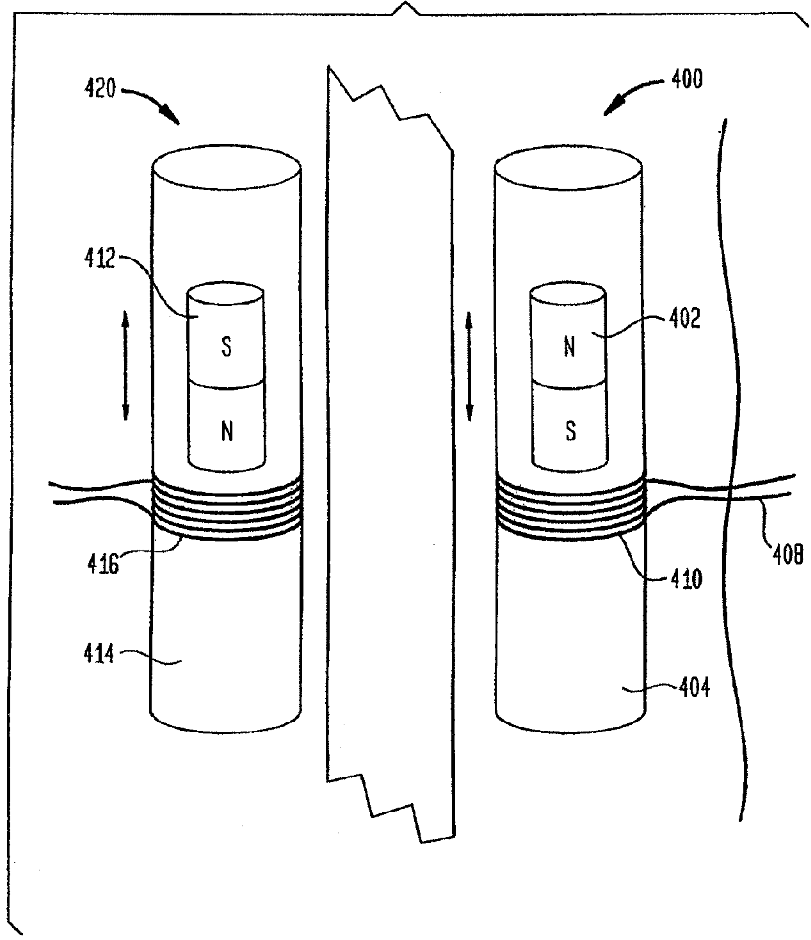
FIG. 4 is a representation of one embodiment of a kinetic motion powering device for powering the food intake restriction system of FIG. 1.

FIG. 4 shows another embodiment of a communicating member in the form of a kinetic motion apparatus 400 adapted to provide power to the implantable restriction device. In one exemplary embodiment, as shown, the kinetic motion apparatus 400 includes a housing having a magnet 402 disposed therein. The housing can be of any shape and made of any material known in the art, but in the illustrated embodiment, the housing is in the form of a glass tube or cylinder 404 having a metal or copper wire 410 wrapped tightly in a coil around an exterior surface of the cylinder 404. In this configuration, the kinetic motion apparatus 400 can generate electricity in the copper wire 406 by movement of the magnet 402 contained within the cylinder 404. Movement of the magnet 402 within the cylinder 404 will effectively cause the copper wire 410 to be moved through a magnetic field, thereby causing electricity to be generated, as will be appreciated by those skilled in the art. Electrical leads 408 coupled to the copper wire 410 are provided to carry the electricity generated by the kinetic motion apparatus 406 to a storage device or directly to devices within the implantable restriction device as needed. A means for monitoring the charge level of the storage device may also be included.

While many configurations are possible, in one exemplary embodiment, the kinetic motion apparatus 400 can be implanted within a patient's body such that physical movement of the body is effective to move the magnet 402 within the cylinder 404. For example, a patient can perform any movement, such as walking, running, jumping, shaking, etc., and this will cause the magnet 402 to move laterally, rotationally, or any combination thereof, within the cylinder 404 to generate electricity within the copper wire 406. In another example, the kinetic motion apparatus 400 may be implanted within a patient's body such that more subtle, but predictable physical movements within the body are effective in moving the magnet 402 within the cylinder 404. Examples of internal movements within the patient that may be harnessed include, but are not limited to, motions related to respiration (e.g., motions of the diaphragm), digestion (e.g., peristaltic waves through any portion of the gastrointestinal tract), and/or oscillatory motions within the circulatory system (e.g., pulsatile flow in the arterial system, motion of the heart, etc.).

Alternatively, or in addition, the kinetic motion apparatus 400 can include an external driver. In the embodiment shown in FIG. 4, the external driver is composed of the same elements as the kinetic motion apparatus 400, namely, a housing 414, a magnet 412, and a copper wire 416 to form an external electromagnet 420. The external electromagnet 420 can be manually driven by supplying the copper wire 416 with electricity to cause the magnet 412 to oscillate. As the magnet 412 oscillates, sympathetic oscillations are induced in the magnet 402 disposed within the kinetic motion apparatus 400, thereby causing electricity to be generated to supply power to the implantable restriction device. A person skilled in the art will appreciate that any driver or vibration element, internal or external, which is effective to produce oscillations, vibrations, or other motions in the magnet 402 within the kinetic motion apparatus 400, can be used to generate power. One additional alternative may include the conversion of oscillatory gradients in pressure created by natural and regularly occurring events such as respiration into fluid flows that induce oscillatory translational and/or rotational motions of the magnet 402. Moreover, the kinetic motion apparatus 400 can have a variety of other configurations in which energy is generated from motion or pressure gradients caused by these motions.

Although not shown in FIG. 4, an external device can also be provided to be in communication with the external driver and it can provide power to the external driver taken from a battery or other power source. The external driver can also include a gauge that indicates a charge status of the communicating member and/or whether there is proper alignment between an external driver and the kinetic motion apparatus 400. For example, the gauge can indicate whether circuitry and/or devices within the implantable restriction device need to be charged by the kinetic motion apparatus 400, or whether they are fully charged. Alternatively or in addition, the gauge can indicate proper alignment of an external driver that is attempting to generate sympathetic oscillations within the kinetic motion apparatus 400. The indication given by the gauge can take the form of any notification means known in the art, including a light, such as an LED, an audible noise, and/or a vibration.

Figure 5:
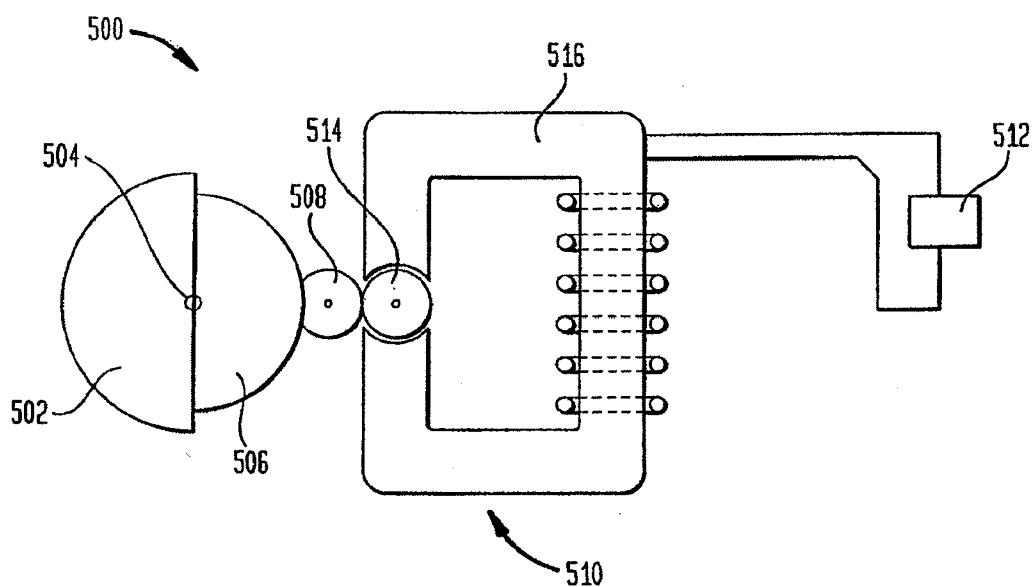
FIG. 5 is a representation of another embodiment of a kinetic motion powering device for powering the food intake restriction system of FIG. 1.

In another exemplary embodiment, a kinetic motion apparatus is provided that is operable to convert motion into energy to power the implantable restriction device. In one embodiment shown in FIG. 5, a kinetic motion apparatus 500 is provided and can include a counterweight 502 coupled to a shaft 504 such that the counterweight 502 can freely pivot about the shaft 504 in response to motion and movement of the patient. The counterweight 502 and the shaft 504 can be formed from any biocompatible material known in the art, including stainless steel, titanium, cobalt chrome, and any number of polymer plastics. A drive gear 506 can be nested within a hollow portion of the counterweight 502, and in one embodiment, it can be directly coupled to the counterweight 502 such the drive gear 506 moves in response to movement of the counterweight 502. The drive gear 506 can also be coupled to a drive train of an electric generator 510. As the drive gear 506 moves in response to the counterweight 502, it rotates a pinion gear 508 which in turn rotates the rotor 514 to a high velocity. This rotation then induces electric current through the stator 516 thereby charging the capacitor 512. The electric generator 510 thus converts mechanical energy from movement of the counterweight 503 into electrical energy.

The electrical energy produced by the generator 510 can be used to directly power the implantable restriction device or it can be stored within an accumulation element 512 for later use. In an exemplary embodiment, the accumulation element 512 can be a capacitor that contains lithium ion which provides an efficient conducting surface that may store energy longer than those capacitors typically made from other substrates. In another embodiment, the accumulation element 512 can be a high density ultracapacitor. A person skilled in the art will appreciate that any combination of gearing can be used to couple a patient's movement to the generator and any type of accumulation element 512 can be used to store charge.

Figure 6:
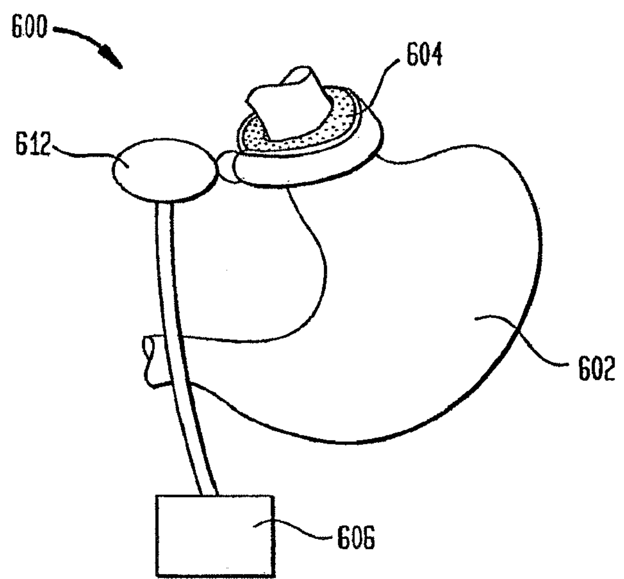
FIG. 6 is a representation of still another embodiment of a kinetic motion powering device for powering the food intake restriction system of FIG. 1.

In another embodiment shown in FIG. 6, a kinetic motion apparatus 600 is provided such that motion of a stomach 602 pushing against fluid in the gastric band 604 is converted into energy to supply power to a rechargeable battery or an accumulation element 606 that stores charge. As food passes through the band 604, pressure will increase and decrease in the gastric band 604. This vibration energy can be harvested by a variety of different methods known in the art such as electromagnetic, electrostatic, or piezoelectric conversion. In piezoelectric (piezo) methods, a bimorph based on piezoelectric materials vibrates, creating a charge that generates a voltage with amplitude proportional to the size and shape of the piezoelectric material, periodicity, and amount of force. Thus, the kinetic motion apparatus 600 can include a piezoelectric transducer element 612 attached to the gastric band 604 that can produce power proportional to the displacement and periodicity of band movement. This energy can then be stored in the accumulation element 606 until needed by the implantable restriction device. A person skilled in the art will appreciate that similar use can be made of electro-active polymer elements attached to the gastric band.

The internal devices disclosed herein are designed to be single use devices. The external devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application. The implantable devices disclosed herein are designed for single patient use.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system for forming a restriction in a patient, comprising:

an implantable restriction device adapted to form a restriction in a patient, the implantable restriction device including a fluid injection port configured to allow fluid to be introduced into and removed from the restriction device to alter the amount of restriction provided by the restriction device and a communicating member disposed within the fluid injection port and adapted to receive light waves and to convert the light waves into energy that powers the implantable restriction device.

2. The system of claim 1, further comprising an external energy transfer apparatus having a light source operable to communicate the light waves to the communicating member.

3. The system of claim 2, wherein the external energy transfer apparatus includes a gauge effective to indicate whether the light waves are being communicated between the light source and the communicating member effective to power the implantable restriction device.

4. The system of claim 2, wherein the light source emits light selected from the group consisting of infrared light waves in a range of about 0.75 μm to 1,000 μm, visible light waves in a range of about 400 nm to 750 nm, and ultraviolet light waves in a range of about 280 nm to 400 nm.

5. The system of claim 1, wherein the communicating member comprises a photovoltaic cell array or silicon nanowire bundle.

6. The system of claim 1, wherein the communicating member comprises a crystalline silicon cell array.

7. The system of claim 1, wherein the implantable restriction device comprises a the gastric band and a housing in communication with the gastric band.

8. The system of claim 7, wherein the communicating member is disposed in the housing.

9. The system of claim 1, wherein the communicating member is configured to receive and transmit data.

10. A method for providing power to an implantable restriction device, comprising:

activating a light source to transfer light through tissue to a communicating member disposed within a fluid injection port of an implantable restriction device implanted in a patient to form a restriction in a pathway, the communicating member converting the light to electrical power or energy to power the implantable restriction device.

11. The method of claim 10, wherein the light source is on an external device, and the method further comprises positioning the external device adjacent to a skin surface and in proximity to the communicating member implanted within tissue.

12. The method of claim 11, wherein the external device receives data from the communicating member, the data including at least one measurement of pressure of fluid within the implantable restriction device.

13. The method of claim 11, wherein the external device includes a gauge that indicates whether the light being transferred between the light source and the communicating member is effective to power the implantable restriction device.

14. The method of claim 10, wherein the communicating member comprises a photovoltaic cell array or silicon nanowire bundle.

15. The method of claim 10, wherein the communicating member comprises a crystalline silicon cell array.

16. The method of claim 10, wherein the light source emits light selected from the group consisting of infrared light with a wavelength in a range of about 0.70 μm to 1,000 μm, visible light with a wavelength in a range of about 400 nm to 750 nm, and ultraviolet light with a wavelength in the range of about 280 nm to 400 nm.

17. The method of claim 10, wherein the implantable restriction device comprises a gastric band disposed around a stomach to form a restriction, and a housing in communication with the gastric band.

* * * * *